United States Patent
Whitmore et al.

(10) Patent No.: US 6,929,621 B2
(45) Date of Patent: Aug. 16, 2005

(54) DRAINAGE CATHETER WITH BIFURCATING TIP

(75) Inventors: Willet F. Whitmore, Sarasota, FL (US); Winston E. Barzell, Sarasota, FL (US); Roger F. Wilson, Sarasota, FL (US)

(73) Assignee: CIVCO Medical Instruments Co., Inc., Kalona, IA (US)

(*) Notice: Subject to any disclaimer, the term of this patent is extended or adjusted under 35 U.S.C. 154(b) by 82 days.

(21) Appl. No.: 10/261,662

(22) Filed: Oct. 2, 2002

(65) Prior Publication Data

US 2004/0068252 A1 Apr. 8, 2004

(51) Int. Cl.[7] .................. A61M 29/00; A61M 5/32; A61M 27/00
(52) U.S. Cl. .................. 604/109; 604/177; 604/544
(58) Field of Search .................. 604/104–109, 604/174, 177, 544

(56) References Cited

U.S. PATENT DOCUMENTS

| | | | |
|---|---|---|---|
| 1,733,189 A | 10/1929 | Friedman | |
| 1,738,152 A | 12/1929 | Porter | |
| 2,078,111 A * | 4/1937 | Weeks | 604/106 |
| 3,507,274 A | 4/1970 | Soichet | |
| 3,533,406 A | 10/1970 | Tatum | 128/130 |
| 4,652,259 A | 3/1987 | O'Neil | 604/54 |
| 4,813,935 A | 3/1989 | Haber et al. | 604/99 |
| 4,981,475 A | 1/1991 | Haindl | 604/174 |
| 4,997,421 A | 3/1991 | Palsrok et al. | 604/174 |
| 5,030,199 A | 7/1991 | Barwick et al. | 600/29 |
| 5,052,998 A | 10/1991 | Zimmon | 604/8 |
| 5,073,166 A | 12/1991 | Parks et al. | 609/93 |
| 5,322,501 A | 6/1994 | Mahmud-Durrani | 604/8 |
| 5,454,365 A * | 10/1995 | Bonutti | 600/204 |
| 5,547,458 A | 8/1996 | Ortiz et al. | 600/204 |
| 5,704,353 A | 1/1998 | Kalb et al. | 128/634 |
| 5,707,357 A | 1/1998 | Mikhail et al. | 604/96 |
| 5,921,944 A | 7/1999 | Borodulin et al. | 601/83 |
| 5,935,107 A * | 8/1999 | Taylor et al. | 604/164.04 |
| 6,254,571 B1 | 7/2001 | Hart | 604/107 |
| 6,508,825 B1 * | 1/2003 | Selmon et al. | 606/198 |
| 6,565,536 B1 * | 5/2003 | Sohn | 604/174 |
| 6,638,247 B1 * | 10/2003 | Selmon et al. | 604/104 |
| 6,689,099 B2 * | 2/2004 | Mirzaee | 604/107 |
| 6,695,813 B1 * | 2/2004 | Boyle et al. | 604/106 |
| 6,702,834 B1 * | 3/2004 | Boylan et al. | 606/200 |
| 2001/0020162 A1 | 9/2001 | Mosel et al. | 604/544 |
| 2001/0041883 A1 | 11/2001 | Devonec | 604/544 |
| 2001/0049492 A1 * | 12/2001 | Frazier et al. | 604/104 |
| 2001/0049494 A1 | 12/2001 | Liu | 604/107 |
| 2002/0045883 A1 | 4/2002 | Jellie | 604/514 |
| 2002/0045886 A1 | 4/2002 | Porter | 604/544 |
| 2002/0049425 A1 | 4/2002 | Mosel et al. | 604/544 |
| 2002/0143292 A1 * | 10/2002 | Flinchbaugh | 604/107 |

FOREIGN PATENT DOCUMENTS

| | | |
|---|---|---|
| JP | 2000189519 | 7/2000 |
| WO | WO 02/00286 A1 | 1/2002 |

* cited by examiner

Primary Examiner—Larry I. Schwartz
Assistant Examiner—Michael G. Bogart
(74) Attorney, Agent, or Firm—Steptoe & Johnson LLP

(57) ABSTRACT

The present invention relates to a catheter that includes an elongate body having distal and proximal ends, the elongate body having at least one lumen therethrough, a distal portion of the elongate body having a perimeter. First and second retention members of the catheter are first and second retention members selectively disposed in either an insertion state or a retention state. In the insertion state, the first and second retention members form a distal body defining a central axis, the central axis being generally spaced apart from the perimeter of the distal portion of the elongate body, the distal body and elongate body insertable along a passageway of a mammal. In the retention state, the first and second retention members are selectively disposed in a spaced apart configuration to resist proximal movement of the catheter along the passage of the mammal.

46 Claims, 23 Drawing Sheets

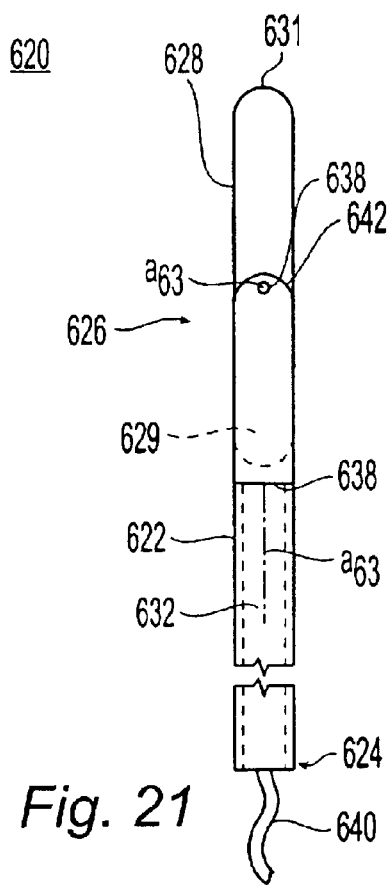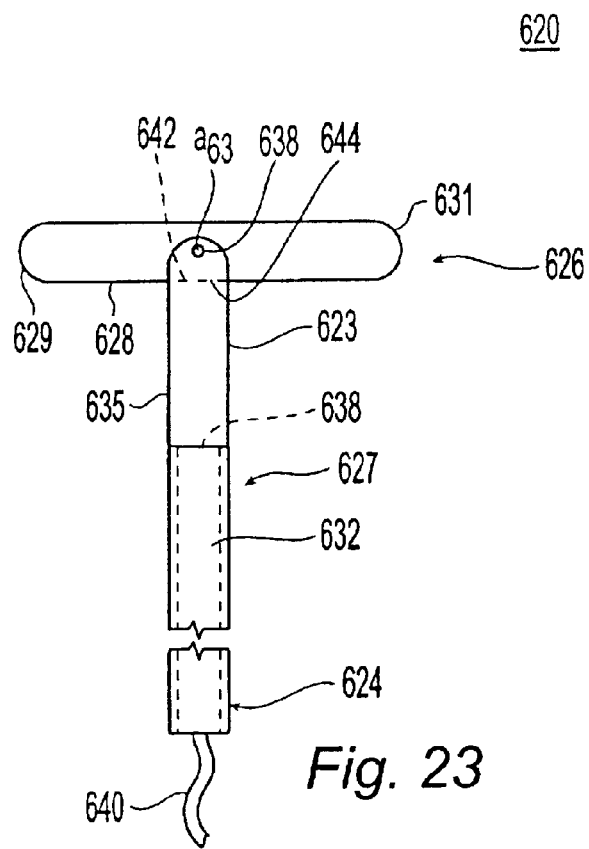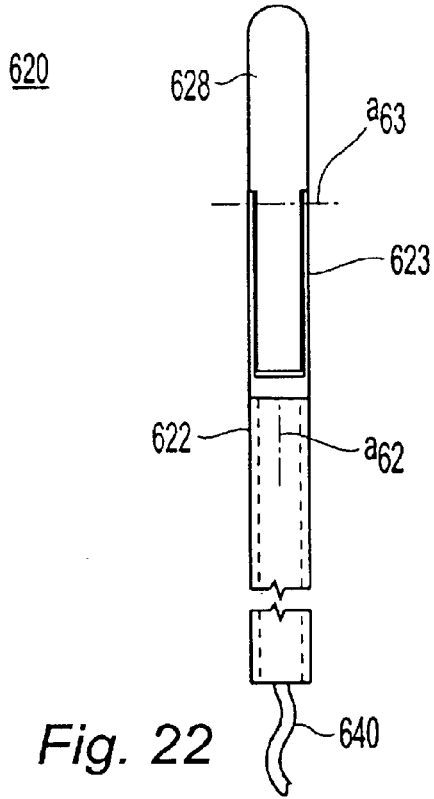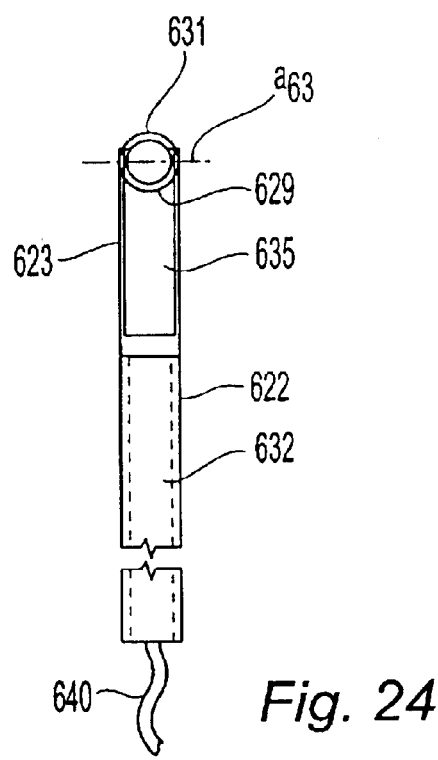
Fig. 21
Fig. 22
Fig. 23
Fig. 24

DRAINAGE CATHETER WITH BIFURCATING TIP

FIELD OF THE INVENTION

The present invention relates to catheters and to retention devices for removably retaining catheters within a body.

BACKGROUND OF THE INVENTION

Urinary catheters may be used to drain urine from the bladder of a catheterized individual. One known catheter, the Foley catheter, includes a balloon located near the tip of a tube sized to pass through the urethra. Once the tip is within the bladder, the balloon is filled with fluid to retain the tip in the bladder. Because the balloon must be bulky in order to retain the catheter tip, many patients experience discomfort when catheterized particularly if the balloon contacts the trigone, which is very sensitive. Moreover, the filled balloon may injure the patient if traumatically withdrawn from the bladder.

There is a need for a catheter that may be disposed within a bladder and retained without retention by a bulky fluid filled balloon. Additionally, there is a need for a catheter that may be inserted and retained in a known orientation, thereby reducing contact with the trigone of the catheterized individual.

SUMMARY OF THE INVENTION

A first embodiment of the invention relates to a catheter, comprising an elongate body having distal and proximal ends, the elongate body having at least one lumen therethrough, a distal portion of the elongate body having a perimeter; first and second retention members, the first and second retention members being selectively disposed in either an insertion state or a retention state, wherein, in the insertion state, the first and second retention members forming a distal body defining a central axis, the central axis being generally spaced apart from the perimeter of the distal portion of the elongate body, the distal body and elongate body insertable along a passageway of a mammal; and in the retention state, the first and second retention members are selectively disposed in a spaced apart configuration to resist proximal movement of the catheter along the passage of the mammal.

The first and second retention members may each include proximal and distal ends, the proximal ends rotatably associated with the distal end of the elongate body. The distal ends of the retention members may be free ends. The distal end of at least one of the first and second retention members may rotate about a rotation axis with respect to the distal end of the elongate body, the rotation axis generally disposed at a proximal end of the retention member. The distal end of each of the first and second retention members may rotate about a respective rotation axis with respect to the distal end of the elongate body, the rotation axes being generally disposed at respective proximal ends of the retention members.

A respective contour of the first and second retention members may remain substantially constant upon movement from the insertion state to the retention state.

The distal end of the catheter may include an opening to the passage, wherein the central axis of the distal portion of the elongate body intersects the opening. An inner surface of the passage may be substantially concentric with an outer surface of the elongate body.

When the first and second retention members are in the retention state, a distance between a distal extent of the retention members and an opening to the passage of the elongate body may be less than about 3 times a maximum radial dimension of the passage, wherein the distance is taken along the central axis of the distal portion of the elongate body.

The first and second retention members may move proximally upon moving from the insertion state to the retention state.

In the insertion position, a distal portion of the first retention member may extend beyond the second retention member, the distal portion of the first retention member having a substantially unbroken surface. When viewed along the central axis of the substantially distal body, the substantially unbroken surface of the first retention member may obscure at least a portion of the second retention member.

The catheter may further comprising a linkage, wherein the first and second retention members are actuated via the linkage. The linkage may comprise a linkage member, the linkage member being rotatably associated with the first retention member and slidably associated with the second retention member. The second retention member may include a stop, which, in the retention state, releasably accommodates an end of the linkage member thereby inhibiting the retention members from returning to the insertion position. The stop and the end of the linkage member are configured to dissociate in response to a predetermined proximal force so that the retention members may return to the insertion state.

The linkage may include first and second linkage members having respective first and second ends, wherein the first end of the first linkage member is rotatably associated with the first retention member, the first end of the second linkage member is rotatably associated with the second retention member, and the respective second ends of the first and second linkage members are rotatably associated with one another.

The linkage may comprise first and second linkage members, the first and second linkage members rotatable with respect to one another about a rotation axis, wherein, as the first and second retention members move between the insertion state and the retention state, the rotation axis translates substantially along the central axis of the distal body. A distal extent of at least one of the first and second retention members may be greater than a distal extent of the linkage.

The linkage may include a linkage member having first and second linkage member ends, a first end of the linkage member is slidably and rotatably associated with the first retention member and the second linkage member end is slidably and rotatably associated with the second retention member.

The catheter may include a flexible enclosure, wherein movement from the insertion state to the retention state is actuated by expansion of the flexible enclosure.

A radial extent of at least one of the first and second retention members may be at least about as great as a length of the retention member.

The distal body may bifurcate upon moving from the insertion state to the retention state.

The catheter may comprise a proximal portion having at least one spatial marker indicative of an orientation of the first and second retention members. At least one spatial marker may be indicative of whether the retention members are aligned with a coronal plane of a human catheterized with the catheter.

The passage may be a urethra. The mammal may be a human.

Another embodiment of the invention relates to a method for catheterizing a mammal, comprising, providing a catheter comprising an elongate body having distal and proximal ends, the elongate body having at least one lumen therethrough, a distal portion of the elongate body having a perimeter; first and second retention members, the first and second retention members being selectively disposed in either an insertion state or a retention state, wherein, in the insertion state, the first and second retention members forming a distal body defining a central axis, the central axis being generally spaced apart from the perimeter of the distal portion of the elongate body, the distal body and elongate body insertable along a passageway of a mammal; and in the retention state, the first and second retention members are selectively disposed in a spaced apart configuration to resist proximal movement of the catheter along the passage of the mammal; inserting the catheter along a passageway of the mammal until first and second retention members of the catheter enter a cavity of the mammal; and moving the retention members from an insertion state to a retention state, whereby the first and second retention members are removably retained within the cavity.

Still another embodiment of the present invention relates to a urethral catheter for catheterizing a bladder of a human having a coronal plane. The urethral catheter comprises an elongate body having a distal portion and a proximal portion, the elongate body having a passage therealong; first and second retention members movably associated with the distal portion of the elongate body, the first and second retention member movable between an insertion state and a retention state, wherein, in the retention state the first and second retention members extend radially and substantially along a single plane from the elongate body; and the proximal portion of the elongate body includes at least one spatial marker indicative of the whether the first and second retention members are generally aligned with the coronal plane of the human when the first and second retention members are in the bladder of the human.

The first and second retention members may include respective distal outer surfaces, and wherein the respective distal outer surfaces define an angle of at least about 80 degrees with respect to a central axis of the distal portion of the elongate body.

Yet another embodiment of the present invention relates to a urinary catheter retention device for insertion along a urethra into a bladder of a human to releasably retain a passage of an elongate body in fluid communication with the bladder, the retention device comprising a base operably securable to an end of the elongate body; first and second retention members movably associated with the base and having respective free distal ends, the free distal ends of the retention members movable between an insertion state and a retention state, wherein, in the insertion state, the first and second retention members cooperate to form a body, the body being insertable along the urethra; and in the retention state, the free distal ends are spaced apart from one another to resist proximal movement of the elongate body along the passage of the mammal.

Yet another embodiment of the invention relates to a urethral catheter, comprising an elongate body, the elongate body having at least one lumen therethrough; a first retention member, the first retention having first and second ends and being selectively disposed in either an insertion state or a retention state, wherein, in the insertion state, the first and second ends of the retention member are generally aligned with the elongate body so that at least a portion of the catheter is insertable along a urethra of a mammal; and in the retention state, the first and second ends of the retention member are spaced apart from the elongate body to resist proximal movement of the retention member along the urethra of the mammal.

A generally medial portion of the retention member may be rotatably associated with the catheter.

The catheter may include at least one tension member that urges a generally medial portion of the retention member toward a distal end of the catheter.

An axial distance between the generally medial portion of the retention member and a distal end of the elongate body may decrease by at least about one half upon moving from the insertion state to the retention state.

Still another embodiment of the invention relates to a urethral catheter, comprising an elongate body having a distal end and a proximal end and at least one lumen therethrough; at least a first retention member, the at least first retention member being generally associated with the distal end of the elongate body and selectively disposed in at least an insertion state and a retention state, wherein, in the insertion state, the at least first retention member is generally aligned with the elongate body and insertable along a urethra of a mammal; and, in the retention state, at least a portion of the at least first retention member is radially spaced apart from the elongate body, wherein, upon the application of a force of less than about 10 Newtons directed generally proximally along the elongate body, the at least one retention member resists proximal movement of the catheter along the urethra and, upon the application of a force of less than about 25 Newtons directed generally proximally along the elongate body, the at least one retention member returns to an insertion state to permit withdrawal of the catheter along the urethra.

Upon the application of a force of less than about 20 Newtons directed generally proximally along the elongate body, the at least one retention member may return to an insertion state to permit withdrawal of the catheter along the urethra.

Upon the application of a force of less than about 15 Newtons directed generally proximally along the elongate body, the at least one retention member may return to an insertion state to permit withdrawal of the catheter along the urethra.

BRIEF DESCRIPTION OF THE DRAWINGS

The present invention is discussed below with reference to the drawings, in which:

FIGS. 21 and 22 show a sixth embodiment of a catheter of the present invention, with catheter being configured in an insertion state;

FIGS. 23 and 24 show the catheter of FIGS. 21 and 22 being configured in a retention state;

DETAILED DESCRIPTION OF THE INVENTION

Figure 1:
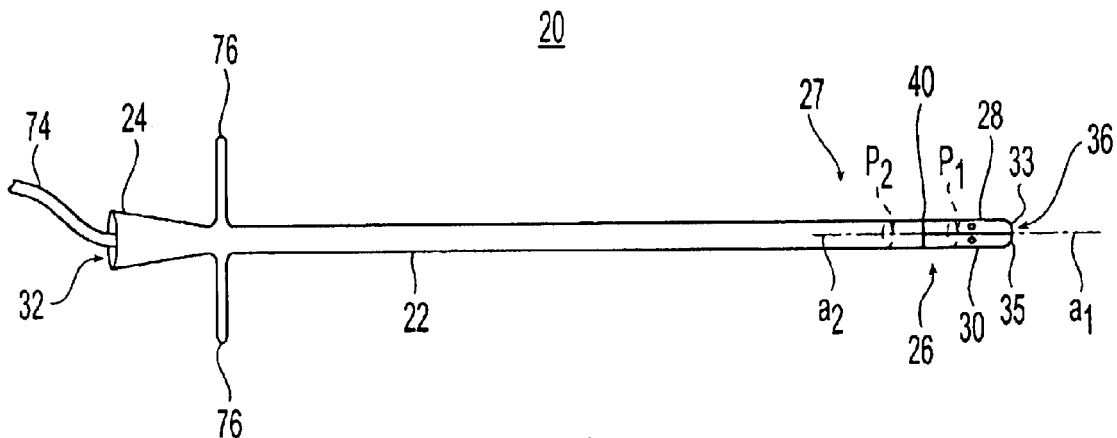
FIG. 1 shows a first embodiment of a catheter of the present invention, the catheter being configured in an insertion state.
Figure 2:
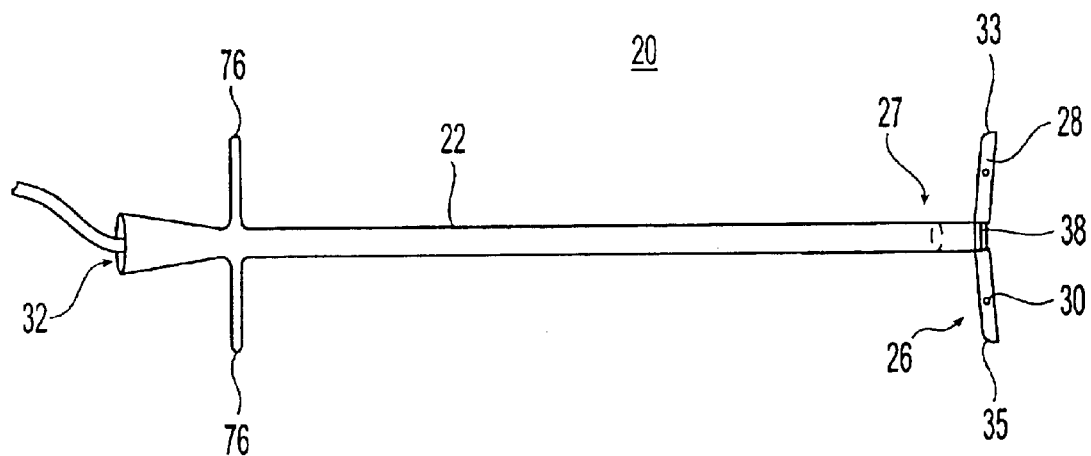
FIG. 2 shows the catheter of FIG. 1, the catheter being configured in an retention state.

Referring to FIGS. 1 and 2, a catheter 20 of the present invention is shown including an elongate body 22. Catheter 20 has a proximal portion 24 and a distal portion 26. The catheter 20 may be configured in at least either an insertion state or a retention state, as shown in FIGS. 1 and 2, respectively. In the insertion state, catheter 20 is insertable along a passageway or lumen of a mammal until at least a portion of distal portion 26 resides within a cavity of the mammal. In the insertion state, catheter 20 may be removed along the passageway or lumen of a mammal without causing injury thereto. Distal portion 26 preferably includes at least two retention members 28, 30 which are movably associated with catheter 20. In the retention state shown in FIG. 2, at least a portion of at least one of retention members 28, 30 is radially extended, thereby resisting proximal movement of catheter 20 along the passage. In a preferred embodiment, both retention members 28, 30 are radially extended in a retention state.

Catheter 20 has at least one retention member and may have 2, 3, 4 or even more retention members. A preferred embodiment of catheter 20 has 2 retention members that retain the catheter in a body cavity. Movement of retention members in accordance with the present invention from the insertion state to the retention state is an opening movement. In a two-retention member catheter, the retention member opening is a bifurcation. Movement of retention members from the retention state to the insertion state is a closing movement. For example, an operator may actuate a closing movement of radially extending retention members 28, 30 of catheter 20 so that the catheter returns to the insertion state allowing the catheter to be withdrawn along a passageway without causing injury to a catheterized mammal.

With respect to the anatomy of a mammal catheterized with catheter 20, the term distal refers to a location that is farther along the passageway from an exterior opening thereof than is another location disposed closer to the exterior of the passageway. For example, catheter 20 may be inserted along the urethra of a human so that retention members 28, 30 are positioned within the bladder of the human. Upon such an insertion, the bladder and retention members 28, 30 are distal to the external opening of the urethra. With respect to catheter 20, the term distal refers to locations closer to a distal end 36 thereof than to proximal portion 24.

Figure 3:
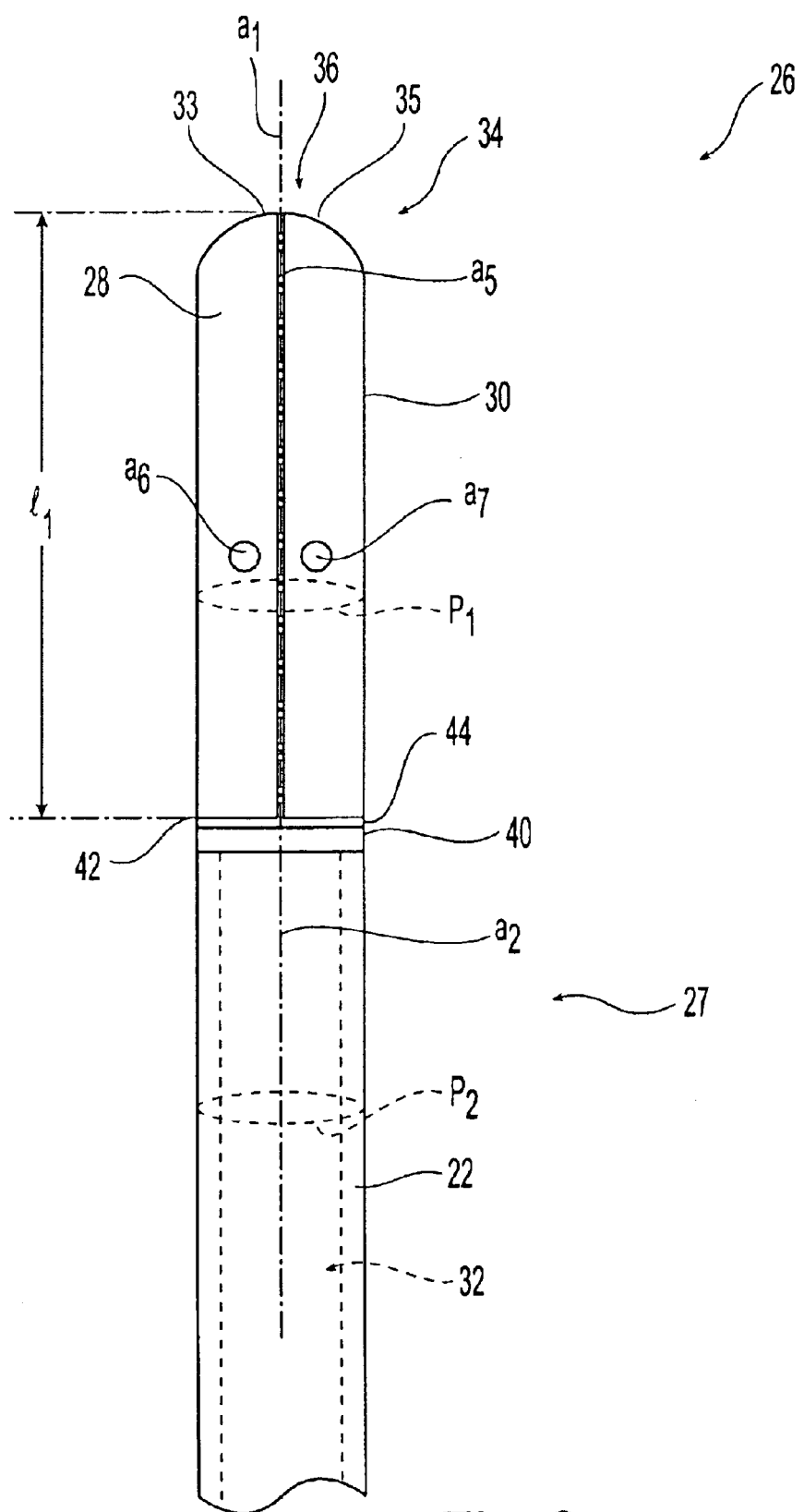
FIG. 3 shows a distal portion of the catheter of FIG. 1 in an insertion state.

Referring to FIG. 3, first and second retention members 28, 30 cooperate in the insertion state to form a distal body 34, which is shaped to allow catheter 20 to be inserted along a passageway. Distal body 34 may be substantially cylindrical, prolate, conical, wedged, spherical, or other suitable configuration for the respective passageway. During the insertion, the distal body 34 is distal to elongate body 22. Thus, insertion of catheter 20 along a passage may also be facilitated by the shape of distal end 36 of distal body 34. Respective retention member distal ends 33, 35 preferably cooperate to form a single substantially blunt surface at distal end 36. Other than distal body 34, distal portion 26 of catheter 20 is preferably free of distally extending projections, such as those that may engage or interfere with portions of the passage as the catheter is inserted therealong.

Distal body 34 defines a distal body axis $a_1$, which is central to a perimeter $p_1$ of distal body 34, as shown in FIG. 3. A distal portion 27 of elongate body 22 defines a distal portion axis $a_2$, which is central to a perimeter $p_2$ a of distal portion 27 of elongate body 22. Distal body axis $a_1$ is preferably spaced apart from perimeter $p_2$. In a preferred embodiment, distal body axis $a_1$ is central to perimeter $p_2$. Distal body axis $a_1$ may be aligned with distal portion axis $a_2$ of distal portion 27 of elongate body 22. It should be understood that, because elongate body 22 may be formed of a flexible material, the relative alignment of distal body axis $a_1$ and distal portion axis $a_2$ may vary. When, however, catheter 20 is straightened so that perimeters $p_1$, $p_2$ are parallel to one another, axes $a_1$, $a_2$ are alignable, as seen in FIGS. 1 and 3.

Figure 4:
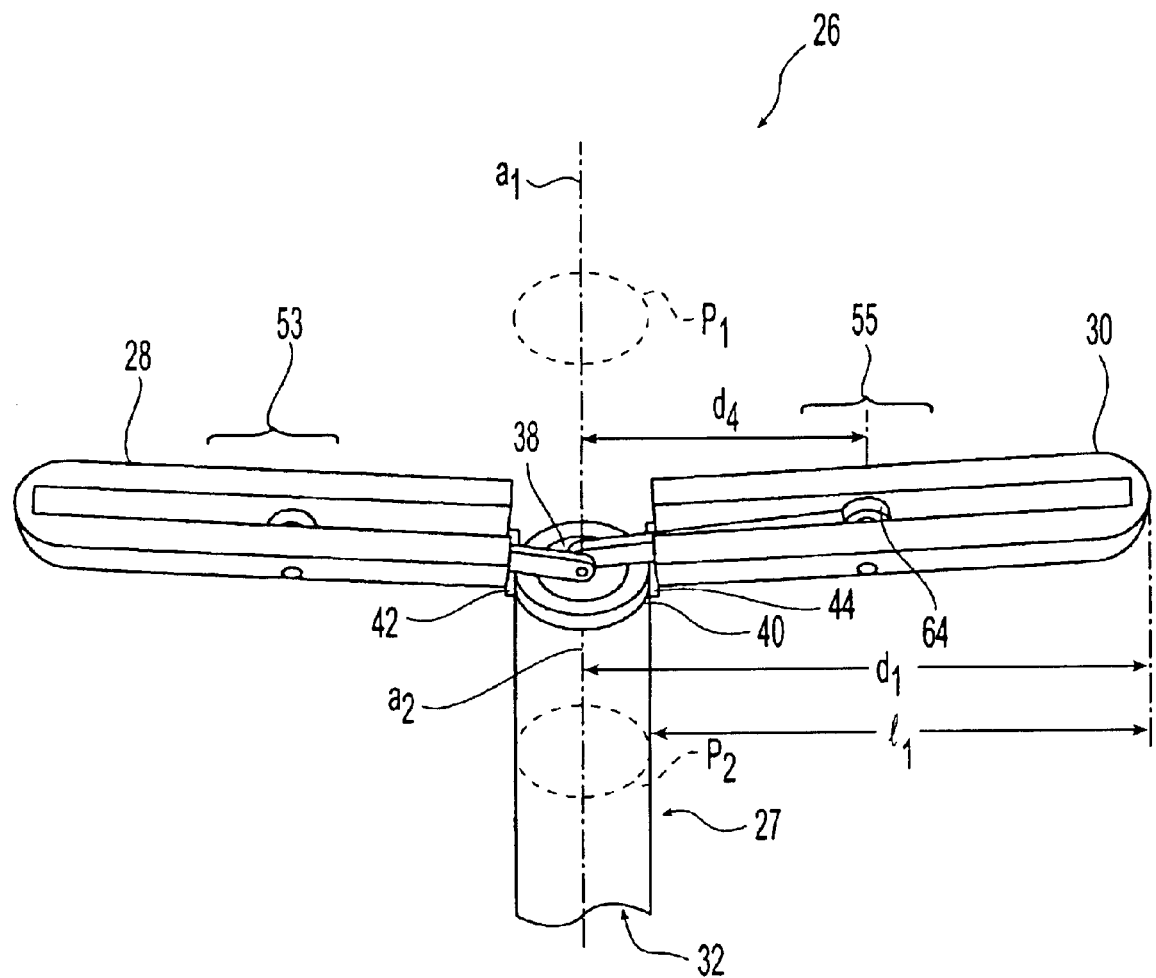
FIG. 4 shows a perspective of a distal portion of the catheter of FIG. 1, the catheter being configured in a retention state.
Figure 5:
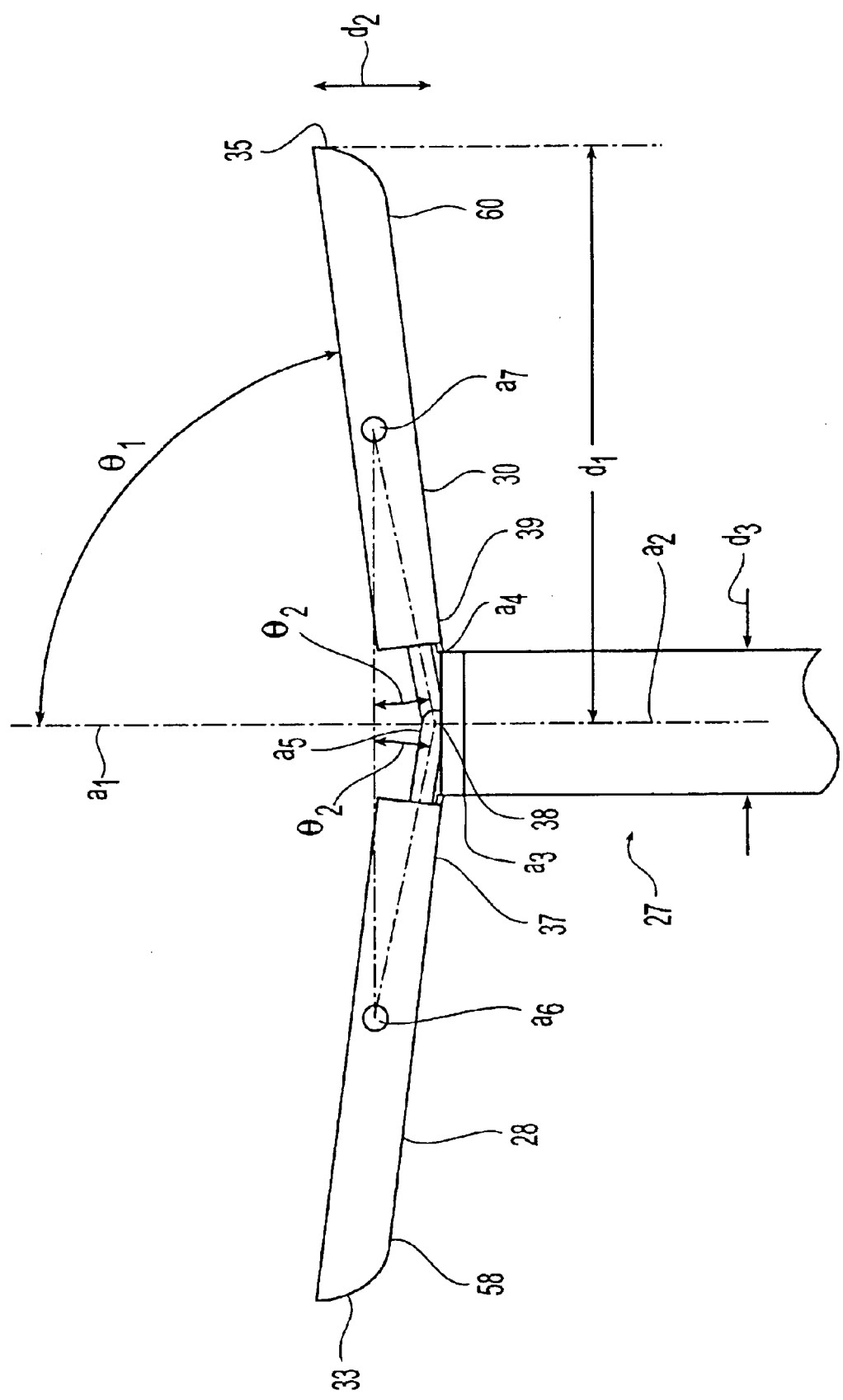
FIG. 5 shows a side view of the catheter of FIG. 4.
Figure 6:
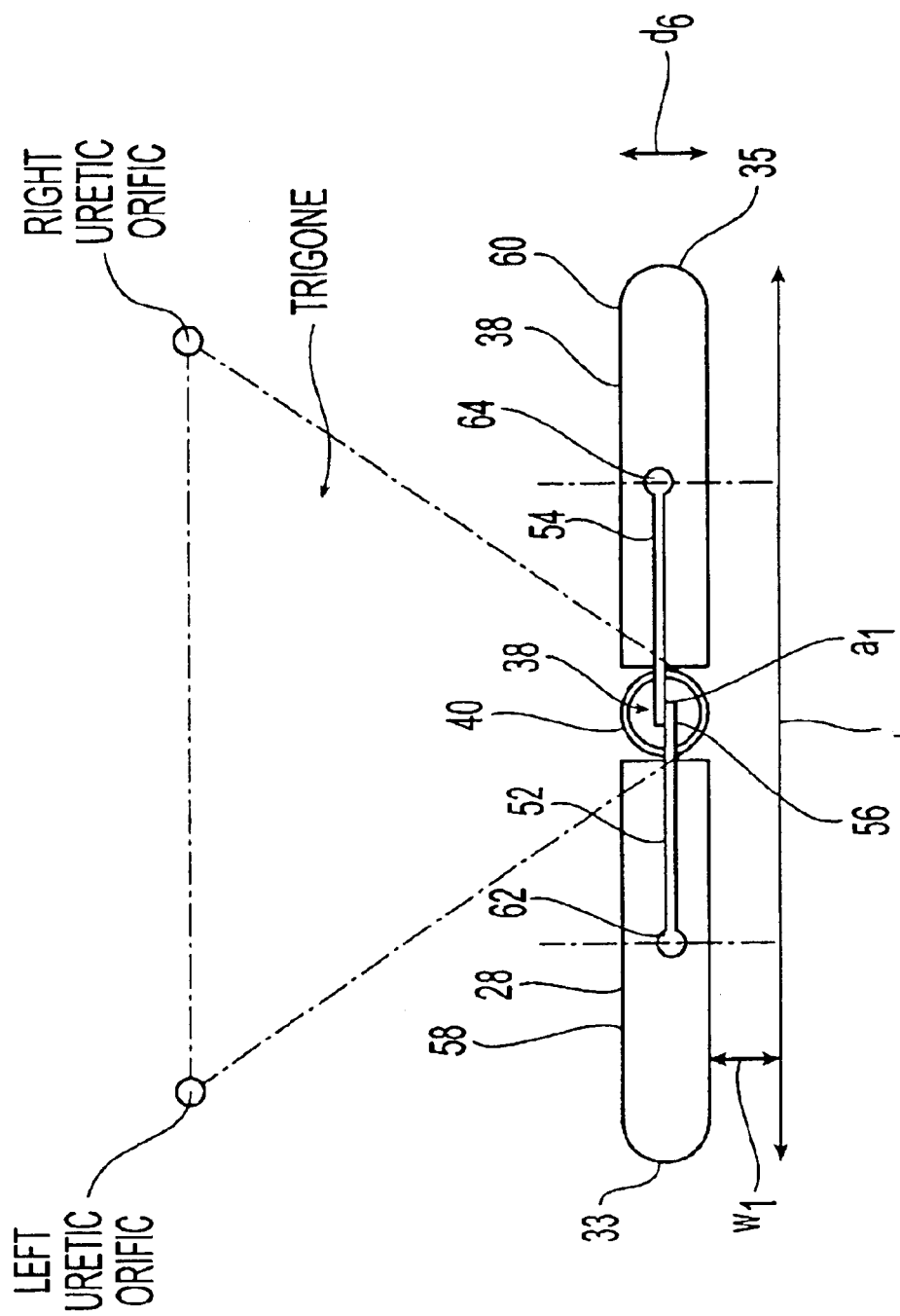
FIG. 6 shows an axial view of the catheter of FIG. 1, the catheter being configured in a retention state in a bladder of a human.

Referring to FIGS. 4–6, the radial extent of first and second retention members 28, 30 increases upon moving from the insertion state to the retention state so that catheter 20 resists proximal movement along a passage when the retention members are within a cavity. Thus, distal retention member ends 33, 35 are spaced apart and retention members 28, 30 no longer cooperate to form distal body 34. In the retention state, a respective radial extent $d_1$ of at least one and preferably both retention members 28, 30 is preferably at least about as great and more preferably greater than a respective retention member length $l_1$. Radial extent $d_1$ is the distance from the maximum radial extent of an end of a retention member to central axis $a_2$. For example, the radial extent $d_1$ of a retention member may be at least about 90%, at least about 100%, or at least about 110% of the length $l_1$ of the retention member. Of course, the radial extent of retention members of catheters of the invention may be different, for example, if either of retention members 28, 30 are rotated farther out from central axis $a_2$. Similarly, the lengths of retention members may be different.

The opening motion of the retention members 28, 30 preferably does not involve bending of respective medial portions 53, 55 of the retention members. Retention members 28, 30 preferably do not compress, such as along axis $a_1$, upon opening. Thus, the respective lengths of retention members 28, 30 are preferably substantially the same in both the insertion and retention states.

A width $w_1$ of retention members 28, 30 may be substantially constant as a function of radial distance along the length thereof. Alternatively, $w_1$ may vary as a function of distance from central axis $a_1$. For example, a width of the retention members may initially increase with radial distance perhaps decreasing toward distal ends of the retention members so that they have a shape that is petaloid, prolate, spheroid, or similar. In the insertion state, the distal body formed by the cooperation of such petaloid or prolate retention members may form a waist or narrower region that is disposed proximal to a distal end of the distal body. Other exemplary retention members have a maximum width at proximal ends thereof and taper to a smaller width at their distal ends.

A lumen 32 runs substantially along an interior length of elongate body 22. When retention members 28, 30 are within a cavity of a mammal, lumen 32 may be in fluid communication with the cavity so that fluid may pass along the lumen between an exterior of the mammal and the cavity. Preferably, fluid may exit the cavity via lumen 32. A distal opening 38, which is preferably disposed at a distal end 40 of elongate body 22, allows fluid to enter lumen 32. For example, urine may exit a bladder of a catheterized mammal. Proximal portion 24, which preferably remains at least partially exposed upon catheterization with catheter 20, may be configured to operatively connect with a drainage system or reservoir so that fluid exiting the cavity may be disposed of or collected.

In the retention state, as seen in FIG. 5, a location of a maximum distal extent of catheter 20 is preferably spaced apart from axis $a_2$ of the distal portion 27 of elongate body 22. For example, a location of maximum distal extent may be determined by respective distal ends 33, 35 of retention members 28, 30. In the retention state, a distance $d_2$ between distal opening 38 and the maximum distal extent of catheter 20 is preferably less than about 6 times, such as less than about 4 times greater than the diameter $d_3$ of distal portion 27 of elongate body 22.

Distal opening 38 is preferably intersected by central axis $a_2$ of distal portion 27 of elongate body 22. Lumen 32 is preferably concentric with elongate body 22. Lumen 32 may be the only lumen passing along the length of the elongate body 22 between the proximal 24 and distal 27 portions thereof. Therefore, the capacity of the lumen 32 to conduct fluid is increased as compared to a catheter having more than one lumen extending therealong.

Figure 7:
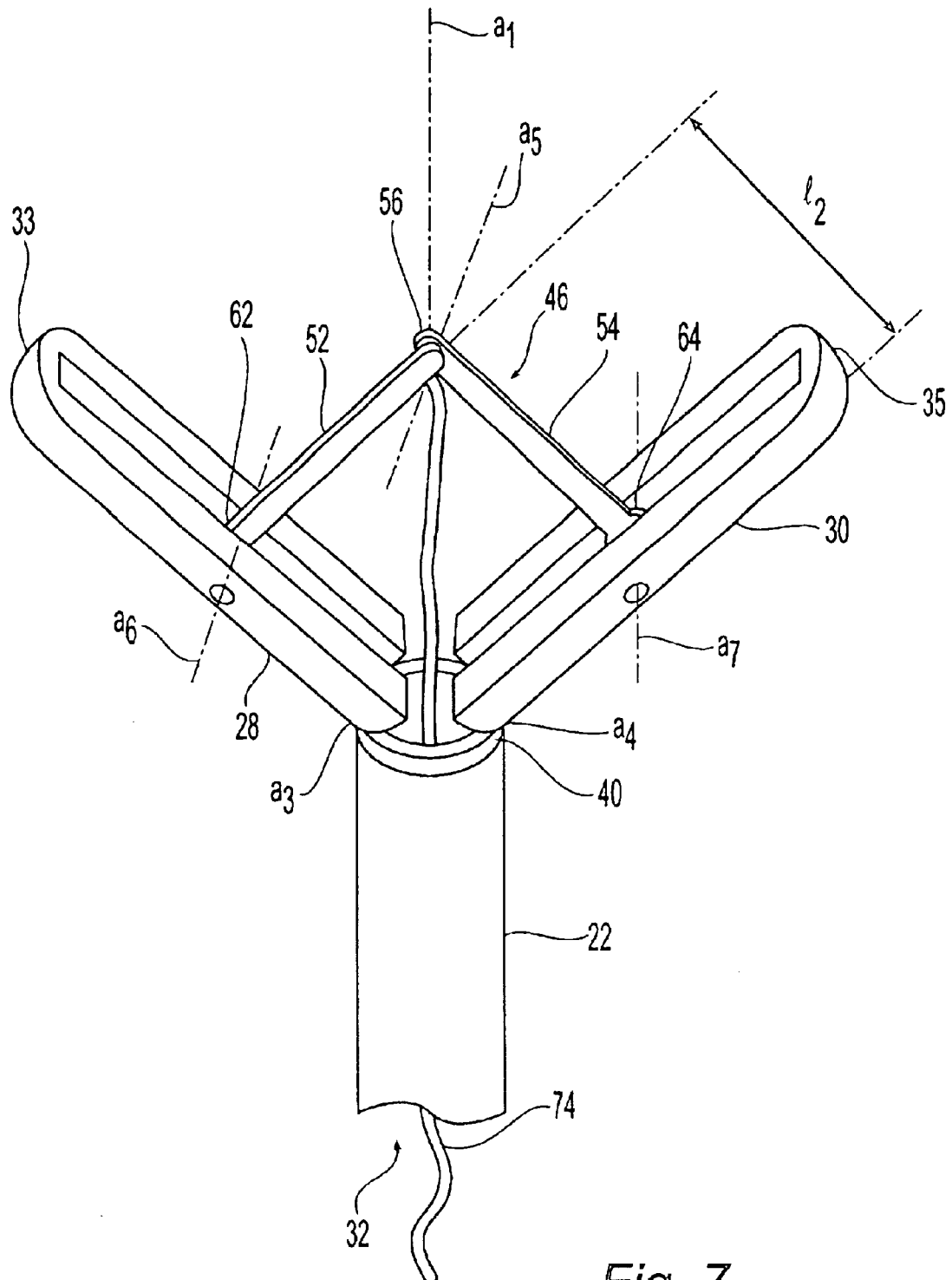
FIG. 7 shows a perspective view of the catheter of FIG. 1, the catheter being configured in a second retention state.
Figure 8:
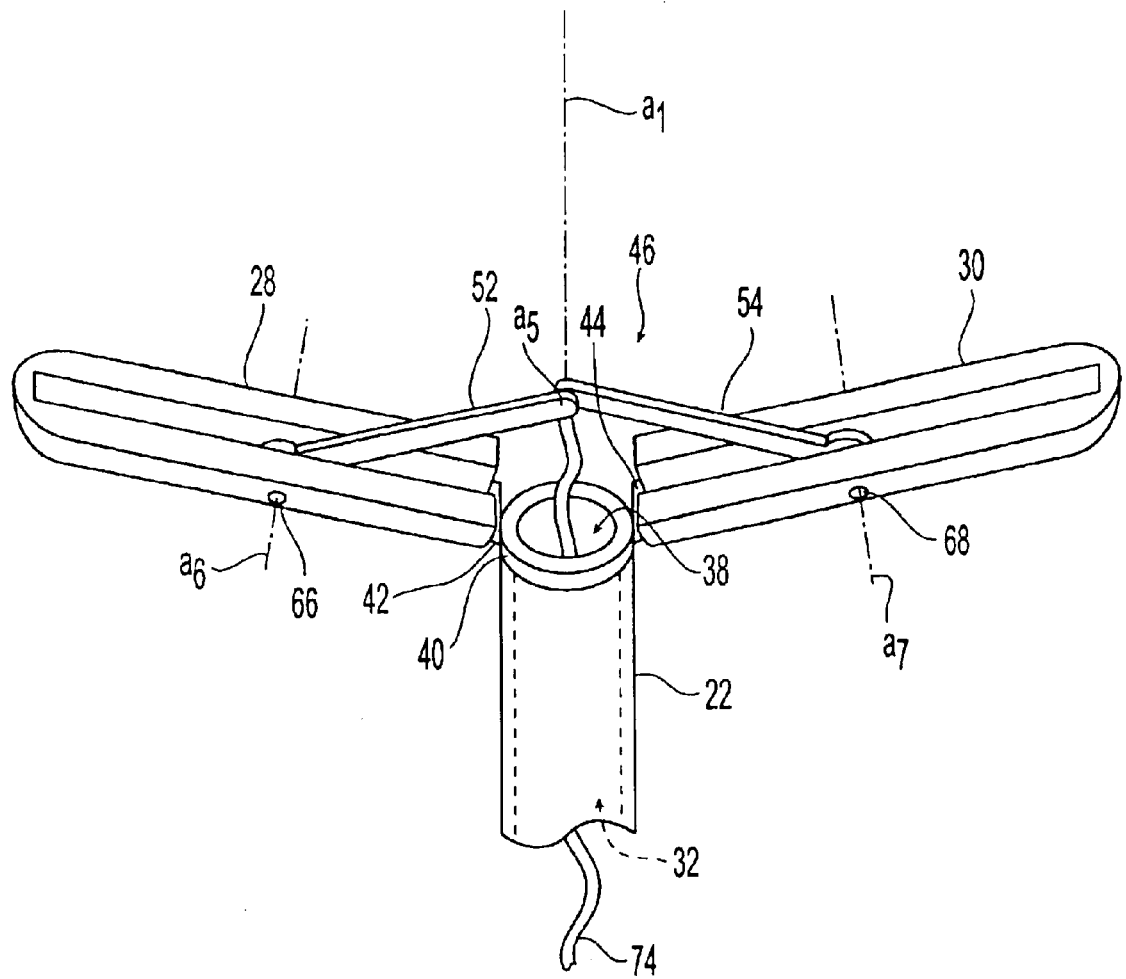
FIG. 8 shows a perspective view of the catheter of FIG. 1, the catheter being configured in a third retention state.

Referring back to FIG. 4 and also to FIGS. 7 and 8, respective distal ends 33, 35 of retention members 28, 30 rotate with respect to elongate body 22 during movement between the insertion and retention states. The distal ends 33, 35 preferably rotate about respective rotation axes $a_3$, $a_4$, which axes are preferably disposed at or adjacent respective proximal ends 37, 39 of retention members 28, 30. Thus, the retention members 28, 30 preferably open and close without bending along their lengths other than any bending that may occur at or adjacent their proximal ends 37, 39. The rotatable association is via respective first and second flexible connections 42, 44, which are preferably capable of repeated bending without damage. The rotatable association of retention members 28, 30 may also be accomplished by other elements, such as pivots or hinges, by which at least one of retention members 28, 30 may rotate with respect to catheter 20. The flexible connections may be secured to catheter 20 by, for example, adhesive, ultrasonic welding, or a mechanical fastener. Alternatively, retention members 28, 30 may be integral with distal portion 27 of elongate body 22 of catheter 20.

Referring back to FIG. 5, respective proximal outer surfaces 58, 60 of retention members 28, 30 define, in the retention state, an angle $\theta_1$ of at least about 65 degrees, preferably at least about 75 degrees, and most preferably at least about 80 degrees with respect to central axis $a_1$ of distal body 34. Angle $\theta_1$ is preferably less than about 115 degrees, such as less than about 100 degrees or even less than about 95 degrees. Thus, with angle $\theta_1$ at least about 75 degrees, the retention members 28, 30 proximally extending and elongate body 22 may be said to define a "T-shape."

As best seen in FIGS. 6 and 7, the first and second retention members 28, 30 may be actuated by a linkage 46. Upon a first actuation motion of linkage 46, retention members 28, 30 move from the insertion state to the retention state. Upon a second actuation motion of linkage 46, retention members 28, 30 move from the retention state to the insertion state.

Linkage 46 includes first and second linkage portions 52, 54 that rotate with respect to one another about a rotation axis $a_5$ at a rotatable connection 56, as seen in FIG. 6. Linkage portions 52, 54 may be of unitary construction or may be formed of separate portions connected by rotatable connection 56. Linkage portions 52, 54 have a length $l_2$, which is less than about 75%, such as less than about 60%, as long as length $l_1$ of retention members 28, 30.

Upon actuation of linkage 46, rotatable connection 56 translates generally linearly along central axis $a_1$ of distal body 34. Rotatable connection 56 may be a pivot having a pivot pin 58 centered upon rotation axis $a_5$. A rotatable connection may instead be formed of a flexible connection that allows the first and second linkage portions 52, 54 to rotate with respect to one another. A rotatable connection may also be a connection in which a portion of one of the linkage members rotates within a portion of the other linkage member. A socket joint in which a convex portion, such as a ball-like portion, of one linkage member rotates within a concave portion, such as a socket, of the other linkage member is an example of such a connection.

First and second linkage portions 52, 54 are rotatably associated with first and second retention members 28, 30, respectively. Upon actuation of linkage 46, linkage portion 52 rotates with respect to retention member 28 about a rotation axis $a_6$ via a rotatable connection 62; linkage portion 54 rotates with respect to retention member 30 about a rotation axis $a_7$ via a rotatable connection 64. Thus, one embodiment of the linkage may include 3 rotatable connections. Rotatable connections 62, 64 are pivots having respective pivot pins 66, 68 centered about respective rotation axes $a_6$, $a_7$. Alternatively, linkage portions 52, 54 may be rotatably associated with respective retention members 28, 30 via flexible connections or socket joints.

In the retention state, a radial distance $d_4$ between one and preferably both of rotatable connections 62, 64 and central axis $a_1$ of distal body 34 is preferably less than the respective radial extent $d_1$ of the one or both retention members 28, 30. Preferably, distance $d_4$ is less than about 80% such as less than about 70% of $d_1$. In the insertion state, a distal extent of one and preferably both retention members 28, 30 is preferably greater than a distal extent of rotatable connection 56 of linkage 46. Therefore, when catheter 20 is viewed along central axis $a_1$ in the insertion state, retention members 28, 30 preferably enclose linkage 46 so that when catheter 20 is inserted, linkage portions 52, 54 do not contact the passage.

In the insertion state, rotation axis $a_5$ of rotatable connection 56 is preferably distal to rotation axes $a_6$, $a_7$ of respective rotatable connections 62, 64. In the retention state, rotation axis $a_5$ is preferably proximal to rotation axes $a_6$, $a_7$. Preferably, a line between one of rotation axes $a_6$, $a_7$ and rotation axis $a_5$ defines an angle $\theta_2$ of at least about 5 degrees and more preferably at least about 10 degrees with respect to a line normal to central axis $a_2$ of distal portion 27. Angle $\theta_2$ is preferably less than about 25 degrees, such as less than about 18 degrees.

In use, an operator may insert catheter 20 along a passage, such as a urethra, until retention members 28, 30 are disposed within a body cavity, such as a bladder. Proximal catheter portion 24 may include one or more radially extending elements 76, which are seen in FIGS. 1 and 2 and prevent over-insertion of catheter 20. Once retention members 28, 30 are disposed within a body cavity, the operator actuates linkage 46 to open the retention members to the retention state. Catheter 20 includes an actuation member 74, which is preferably configured to communicate tension to linkage 46 to actuate the opening motion of retention members 28, 30. In use, actuation member 74 may extend from linkage 46 generally along lumen 32 to proximal portion 24 of catheter 20. An operator may actuate linkage 46 by, for example, applying tension to a proximal portion of actuation member 74. Actuation member 74 may be a filament, fine wire, or other string-like element that may communicate, such as by communicating tension, with linkage 46 for actuation thereof.

When retention members 28, 30 are inserted into a body cavity and moved to the retention state, the retention members preferably resist proximal motion of catheter 20 to thereby maintain fluid communication between passage 38 and the body cavity. In use, however, sudden traumatic forces may be applied to an inserted catheter by, for example, a disoriented patient. A traumatic force is a force sufficient to cause injury to the catheterized individual were the catheter not to return to an insertion state. Therefore, retention members 28, 30 of catheter 20 are configured to return to the insertion state upon the application of such a traumatic force so that catheter 20 may withdraw without causing injury.

To achieve both ordinary retention and injury-free traumatic withdrawal of catheter 20, retention members 28, 30 of catheter 20 preferably resist return to the insertion state with an initial degree of resistance and a later degree of resistance. The initial degree of resistance is greater than the later degree of resistance and may be provided by the configuration of linkage 46. For example, upon the application of a force proximally directed along elongate body 22 when catheter 20 is in the retention state, linkage 46 resists the return of retention members 28, 30 to the insertion state when rotation axis $a_5$ of rotatable connection 56 is proximal to rotation axes $a_6$, $a_7$ of respective rotatable connections 62, 64.

When a traumatic force applied proximally along elongate body 22 overcomes the initial degree of resistance, the configuration of the linkage 46 changes, thereby allowing the retention members 28, 30 to return to an insertion state with a minimum of resistance. By return to an insertion state, it is meant that the catheter returns to a state in which the distal portion of the catheter may pass along a passageway without injury to a catheterized mammal. For example, linkage portions 52, 54 may be configured to disengage one another at rotatable connection 56. Such disengagement may be provided by, for example, a ball-and-socket joint in which the ball-like portion is released from the socket upon the application of a traumatic force. Disengagement may also take place at one of rotatable connections 62, 64. As an alternative to disengagement, one or both of linkage members 52, 54 may be configured to bend or fold up in response to a traumatic proximal force so that retention members 28, 30 may close with a minimum of resistance.

In the retention state, retention members 28, 30 preferably resist proximal movement of catheter 20 for proximally applied forces of less than about 12 Newtons, such as less than about 10 Newtons, for example, less than about 8 Newtons, applied to elongate body 22, but return to an insertion state to permit injury free withdrawal of catheter 20 upon application of a force less than about 25 Newtons, such as a force of less than about 20 Newtons, for example, a force of less than about 15 Newtons. It is understood that a force of about 4.4 Newtons is equivalent to about 1 pound of force.

In its application or use, a catheter of the invention is preferably inserted so that when the one or more retention members extend radially within a bladder, respective proximal outer surfaces of the one or more extended retention members contact a surface of the bladder thereby inhibiting proximal movement of the catheter. For example, as seen in FIG. 5, retention members 28, 30 include proximal outer surfaces 58, 60 that may contact the bladder. Retention members of preferred catheters are preferably configured to minimize contact with the trigone of the bladder. As understood in the art, the trigone is a generally triangular shaped region of the interior of the bladder. The trigone is bounded by respective lines extending from the urethral orifice at the bladder neck to the ureteral orifices and a line extending between the ureteral orifices.

To allow catheter retention with minimal contact with the trigone, catheters of the invention in the retention state preferably have a first radial extent that is greater than a second radial extent of the catheter. For example, retention members 28, 30 of catheter 20 may be retained within a bladder with only minimal or no contact with the trigone. Referring to FIG. 6, a maximum radial dimension $d_5$ of retention members 28, 30 is greater than a minimum radial dimension $d_6$ of the distal portion 26 of the catheter 20. For example, the ratio of the dimensions $d_5$ and $d_6$ may be at least about 3, such as at least about 4, and for example at least about 5. The minimum radial extent $d_6$ may be substantially equal to a diameter $d_3$ of the distal portion 27. When retention members 28, 30 are disposed generally parallel to the coronal plane of a catheterized individual, they essentially avoid contact with the trigone thereby minimizing discomfort to the catheterized individual.

Catheter 20 may include spatial markers indicative of the spatial orientation of retention members 28, 30, when catheter 20 is in a relaxed, substantially untwisted state. The spatial markers allow an operator to determine the orientation of retention members 28, 30 even when these are present within a body cavity. The spatial markers may be the radially extending elements 76, which, when catheter 20 is in the relaxed state, may lie in the same plane as retention members 28, 30, when in the retention state. Indicia, such as surface markings, on proximal portion 24 may also serve as spatial markers.

During insertion, torsional forces may cause catheter 20 to depart briefly from a relaxed orientation such that distal portion 26 twists with respect to the spatial markers. However, when catheter 20 is inserted according to catheterization procedures generally practiced by one in the art, such as with proper lubrication, catheter 20 will return substantially to the relaxed orientation so that the orientation of the spatial markers are indicative of the orientation of retention members 28, 30. Thus, the operator may insert catheter 20, determine whether retention members 28, 30 are disposed along a desired orientation, such as the coronal plane, and extend the retention members. Markers 76 may be releasably fixed with respect to retention members 28, 30 to maintain the desired orientation of the retention members 28, 30. For example, proximal portion 24 and/or markers 76 may be taped to the anterior surface of the thigh or to the lower abdomen.

Figure 9:
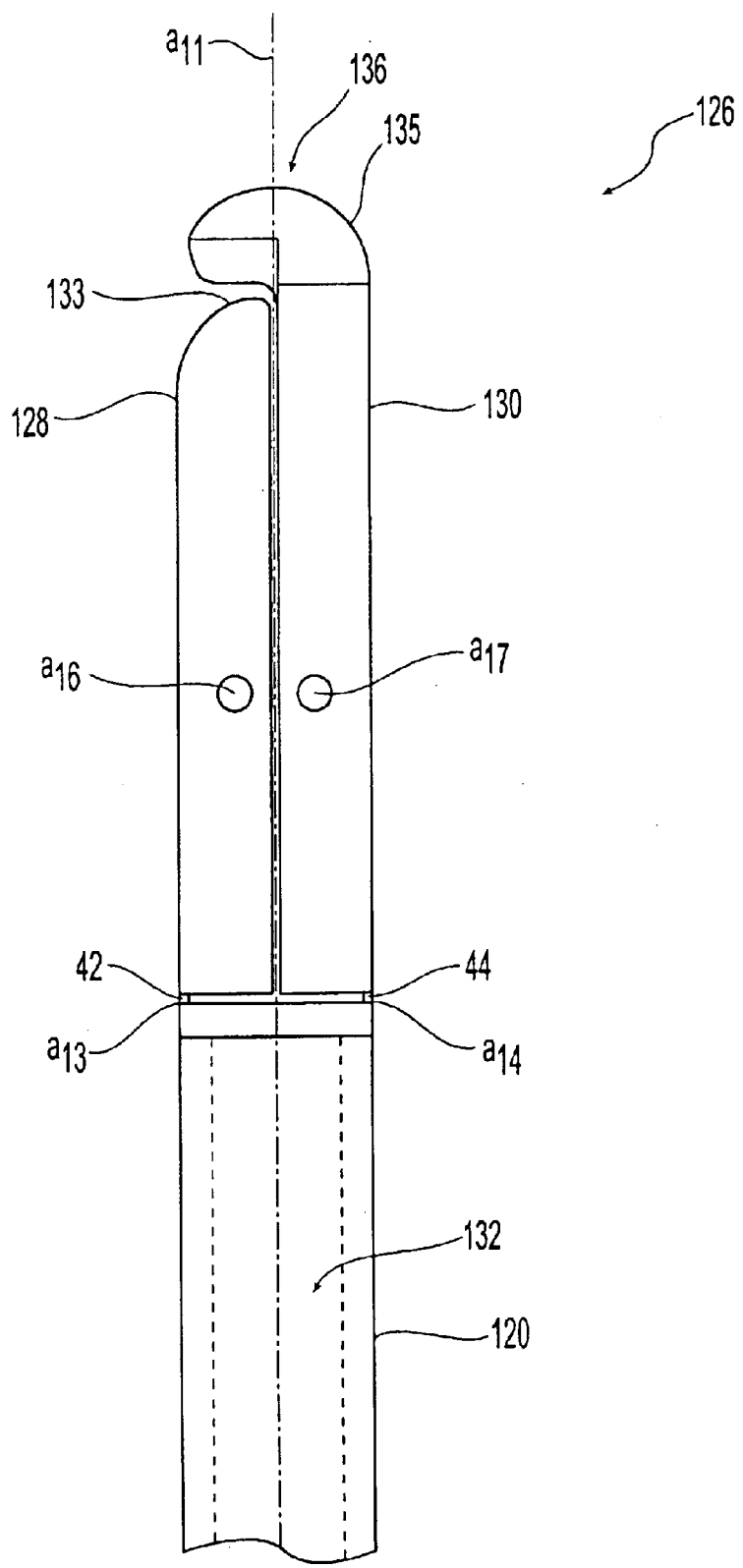
FIG. 9 shows a side view of distal portion of a second embodiment of a catheter of the present invention, the catheter being configured in an insertion state.
Figure 10:
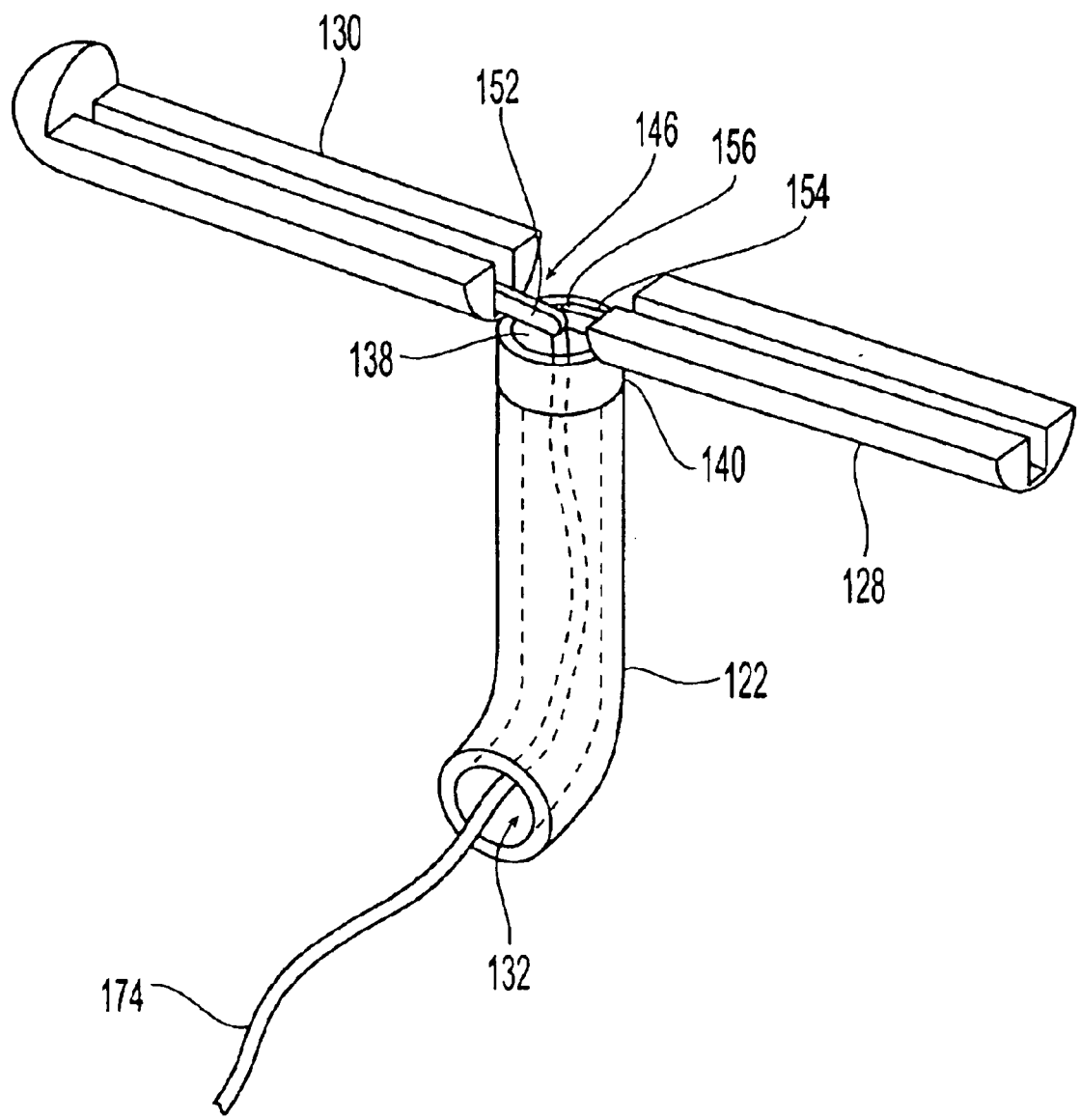
FIG. 10 shows a perspective view of a distal portion of the catheter of FIG. 9, the catheter being configured in a retention state.

Referring to FIGS. 9 and 10, an exemplary embodiment includes a distal portion 126 of a catheter 120 includes first and second retention members 128, 130. In the insertion state, as seen in FIG. 8, retention members 128, 130 cooperate to form a distal body 134 having a central axis $a_{11}$. A distal extent of a distal end 135 of second retention member 130 is greater than a distal extent of a distal end 133 of first retention member 128. When catheter 120 is inserted along a passage, distal end 135 presents a substantially unbroken surface to the passage as retention members 128, 130 progress therealong. Because distal end 135 presents a substantially unbroken surface, forces directed generally against distal end 135 do not tend to urge retention members 128, 130 apart. The distal end 135 preferably obscures or encloses at least a portion of retention member 128 when catheter 120 is viewed along central axis $a_{11}$.

Retention members 128, 130 of catheter 120 function in accordance with retention members of catheters of the present invention. Thus, in the retention state, as seen in FIG. 9, distal ends 133, 135 are spaced apart so that catheter 120 resists proximal motion when retention members 128, 130 are disposed within a body cavity. Fluid may pass along a lumen 132 of an elongate body 122 of catheter 120. Lumen 132 includes a distal opening 138, which is in fluid contact with the body cavity when the retention members 128, 130 are disposed therein. A proximal portion (not shown) of catheter 120 may be identical to proximal portion 24 of catheter 20 so that fluid may be collected or disposed of. Catheter 120 may include spatial markers so that the retention state orientation of retention members 128, 130 may be determined.

Retention members 128, 130 may be actuated in accordance with catheters of the present invention. Thus, for example, a linkage 146 of catheter 120 includes a rotatable connection 156 at which first and second linkage portions 152, 154 rotate via respect to one another. Linkage portions 152, 154 are preferably rotatably connected with respective retention members 128, 130. Rotatable connections of linkage 146 may be pivots, flexible connections, ball-and-socket joints, or other connection about which two portions may rotate relative to one another.

Figure 11:
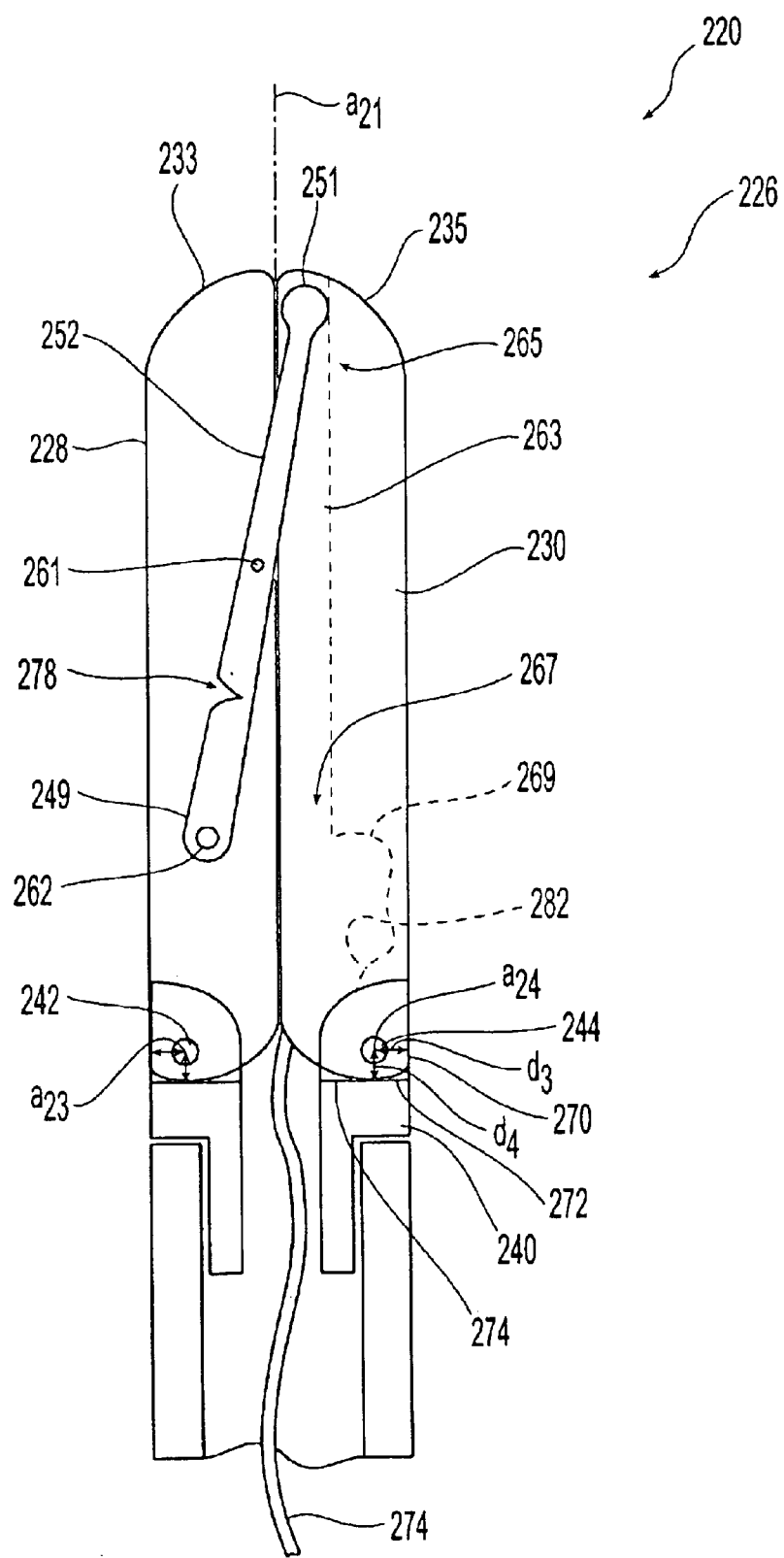
FIG. 11 shows a cross-sectional side view of a distal portion of a third embodiment of a catheter of the invention, the catheter being configured in an insertion state.
Figure 12:
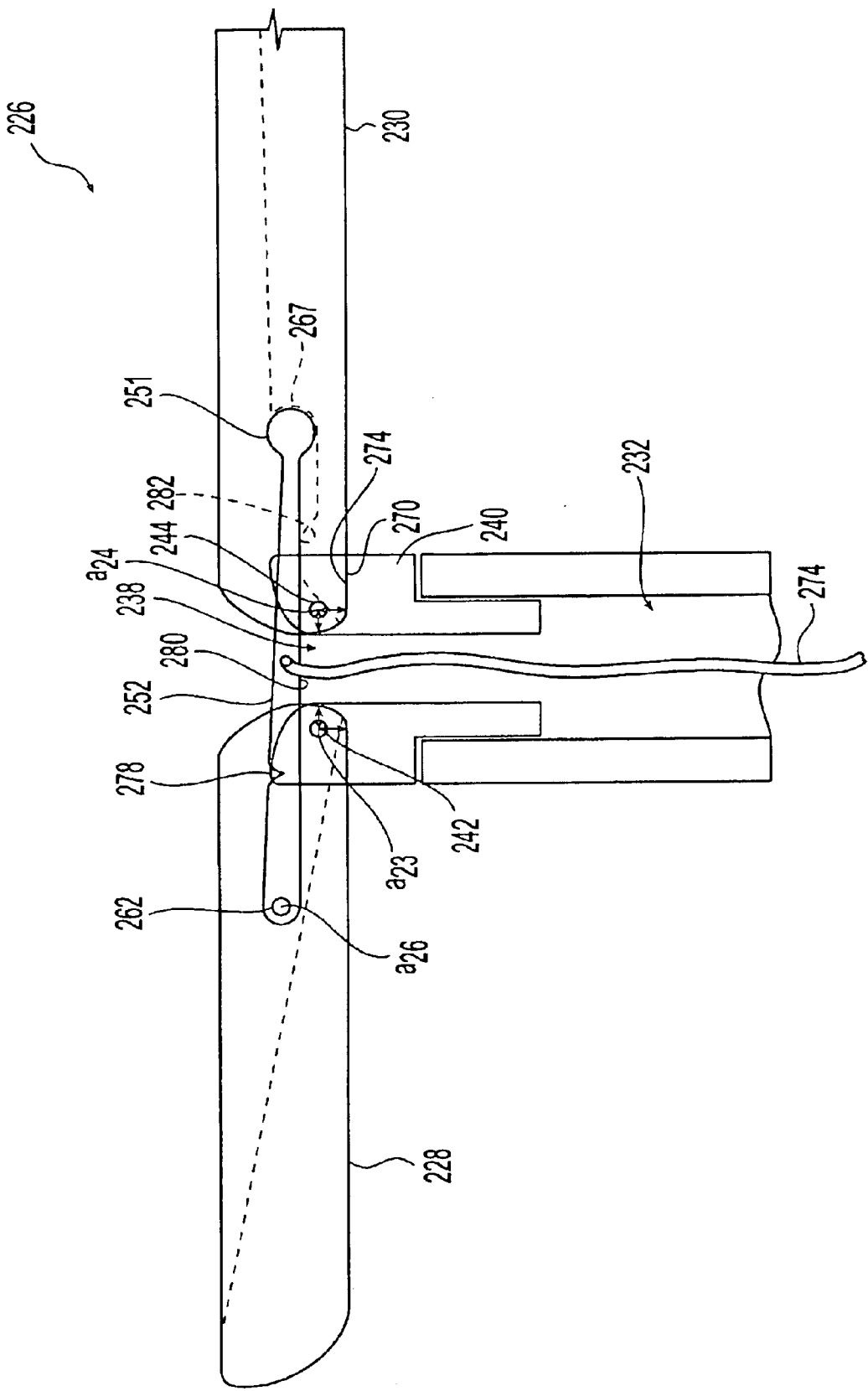
FIG. 12 shows a cross-sectional side view of a distal portion of the catheter of FIG. 11, the catheter being configured in a retention state.

Referring to FIGS. 11 and 12, a distal portion 226 of a catheter 220 includes first and second retention members 228, 230, which rotate with respect to catheter 220 about respective axes $a_{23}$, $a_{24}$. The rotatable association of the retention members 228, 230 is accomplished by respective first and second pivots 242, 244 but may also be accomplished by other rotatable elements such as flexible connections between the retention members and elongate body 222.

In an insertion state, as seen in FIG. 11, retention members 228, 230 cooperate to form a distal body 234 having a central axis $a_{21}$. Upon a first actuation motion, the retention members 228, 230 move from the insertion state to a retention state, as seen in FIG. 12, in which the retention members are spaced apart so that catheter 220 resists proximal movement when the retention members are disposed in a body cavity. Upon a second actuation motion, the retention members 228, 230 move from the retention state to the insertion state. An actuation motion of a linkage 246 actuates movement of retention members 228, 230 from the insertion state to the retention state. Linkage 246 includes a linkage member 252 having first and second ends 249, 251.

The opening motion of retention members 228, 230 may be actuated by applying tension to linkage member 252, such as by a tension member 274. The tension member 274 preferably extends from an attachment point 261 of the linkage member 252 to the proximal portion of catheter 220. Upon actuation of linkage 246, first linkage member end 249 rotates with respect to retention member 228 about a rotation axis $a_{26}$ via a rotatable connection, which is a pivot 262. The rotatable connection may also be, for example, a flexible connection or a ball-and-socket connection.

Second retention member 230 includes a captivating channel 263 having first and second ends 265, 267. Upon actuation of linkage 246, second linkage member end 251 slides generally along captivating channel 263 from the first end 265 to the second end 267 thereof. When a radial extent of first and second retention members 228, 230 is sufficient to resist proximal movement along the passage, second linkage member end 251 releasably associates with a stop 269, as shown in FIG. 11, disposed at the second captivating channel end 267. Stop 269 is preferably at least partially complementary in shape to second linkage member end 251. The releasable association of second linkage member end 251 and stop 269 resists a return motion of second linkage member end 252 from second captivating channel end 267 to first captivating end 265. Thus, in the absence of a traumatic proximal force, catheter 220 remains inserted with the retention members disposed in the body cavity. Linkage member 252 and stop 269 may be characterized as a detent.

To reduce unintentional dissociation of second linkage member end 251 and stop 269, it is desirable that a compressive force be exerted generally along linkage member 252 and stop 269. The compressive force preferably increases friction between second linkage member end 251 and stop 269. Thus, absent a traumatic proximal force, second linkage member end 252 and stop 269 remain associated. To achieve the compression, one or both of first and second members 228, 230 may be urged to rotate about respective axes $a_3$, $a_4$ as if to return to the insertion state, thereby providing compression along second linkage member 252 between rotatable connection 262 and stop 269.

One or both of the retention members 28, 30 may be urged to rotate toward the insertion state via the expansion of a compressed resilient material or the contraction of a resilient material under tension. For example, a distance $d_{24}''$ between rotational axis $a_{24}$ and a shoulder 270 of second retention member 230 is greater than a distance $d_{25}$ between rotational axis $a_{24}$ and a proximal end 272 of second retention member 230. A distal end 240 of catheter 220 has a shoulder 274 comprising a resilient material such as surgical rubber. As second retention member rotates into the fully opened state, retention member shoulder 270 contacts catheter shoulder 274, thereby compressing shoulder 274. The compression urges second retention member 230 to rotate in the opposite direction about axis $a_{24}$, thereby applying the compressive force along second linkage member 252.

Application of a traumatic proximal force to catheter 220 causes retention member 228, 230 to return to the insertion state thereby allowing catheter 220 to withdraw along the passage without causing injury. Linkage member 252 may be constructed of resilient material, which allows a bending motion of the linkage member upon the application of a traumatic force. The bending motion causes second linkage member end 251 and stop 269 to disengage. Linkage member 252 may include a portion having a lowered resistance to bending than other portions of the linkage member. Upon the application of a traumatic force, the linkage member 252 preferentially bends at the portion with lowered bending resistance. For example, linkage member 252 has a lowered resistance to bending about a notch 278 than about other portions of the linkage member.

Retention members 228, 230 may be returned to the insertion state by intentionally disengaging second linkage member end 251 and stop 269. Such dissociation may be accomplished by exerting a distally directed force against a portion of linkage member 252. For example, an operator may insert a stylet or trocar generally along the lumen 232 of catheter 220 and press against a midpoint 280 of linkage member 252, which may bend about a shoulder 282 adjacent captivating channel 263. Once the second linkage member end 251 and stop 269 dissociate, retention members 228, 230 return readily to the insertion state allowing the withdrawal of catheter 220.

Figure 13:
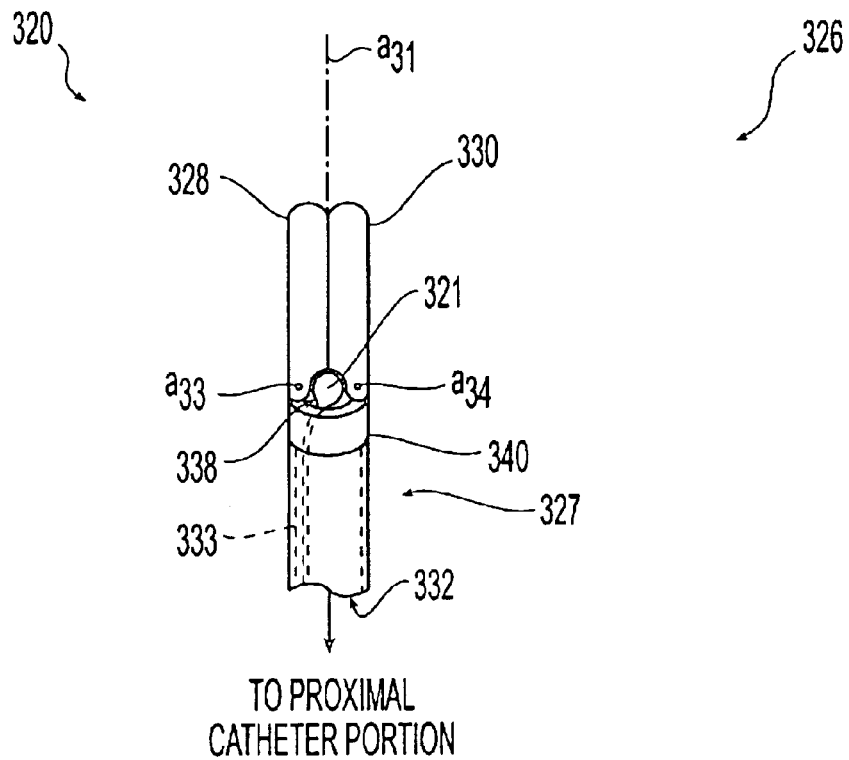
FIG. 13 shows a side view of a distal portion of a fourth embodiment of a catheter of the invention, the catheter being configured in an insertion state.
Figure 14:
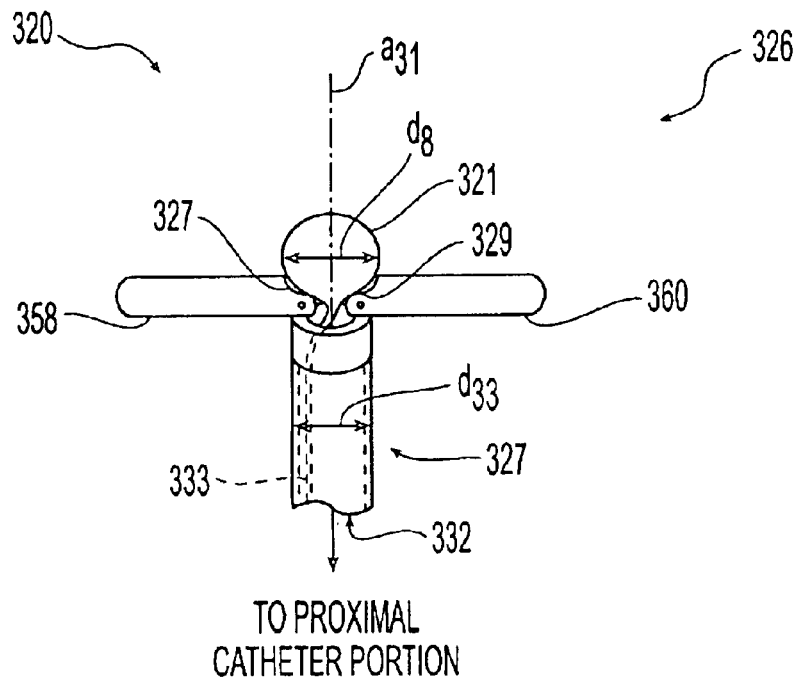
FIG. 14 shows a side view of a distal portion of the catheter of FIG. 13, the catheter being configured in a retention state.

Referring to FIGS. 13 and 14, a catheter 320 includes an enclosure 321 and at least first and second retention members 328, 330. Retention members 328, 330 may be disposed in at least an insertion state, as seen in FIG. 13, and a retention state, as seen in FIG. 14. An opening motion of retention members 328, 330 is preferably actuated by expansion of the enclosure 321, such as with a fluid, such as a gas or liquid. Saline is a preferred fluid. A closing motion of retention members 328, 330 is preferably actuated by release of fluid from enclosure 321. Upon opening or closing, retention members 328, 330 preferably rotate about rotation axes $a_{33}$, $a_{34}$ with respect to catheter 320. Rotatable association of retention members 328, 330 and catheter 320 may be accomplished by, for example, pivots, hinges, flexible connections, socket joints, or other rotatable connection.

Figure 15:
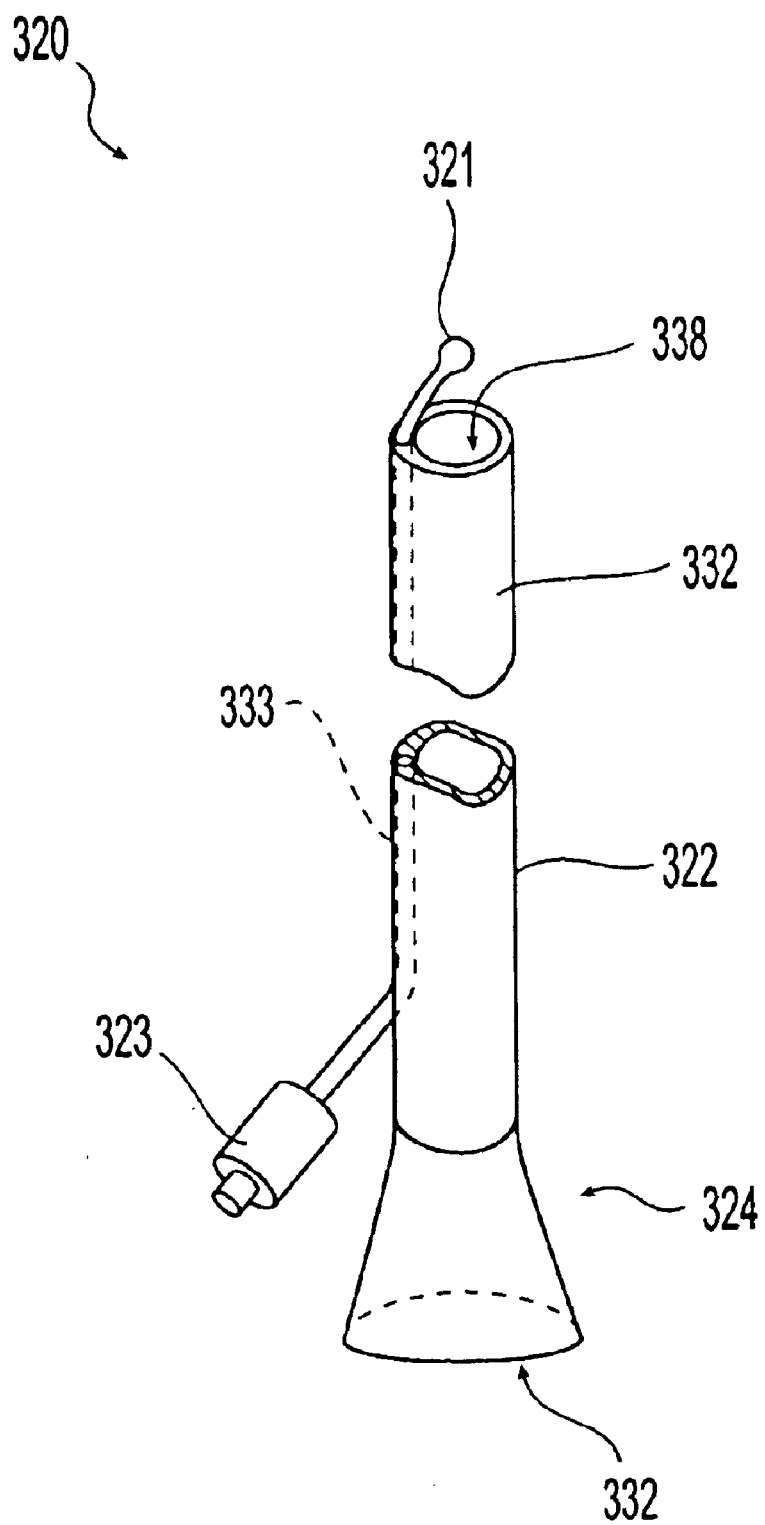
FIG. 15 shows a perspective view of an elongate body of the catheter of FIG. 13, retention members of the catheter not being shown.

Referring also to FIG. 15, a proximal portion 324 of catheter 320 includes a port 323 in fluid communication with a lumen 333, which extends from port 323 to enclosure 321. Port 323 may be any element that allows the introduction of fluid into lumen 333. For example, the fitting may be compatible with a syringe so that the syringe may be used to inject fluid along lumen 333. Fluid entering lumen 333 expands enclosure 321, which expansion exerts a preferably axial force upon retention members 328, 330 to extend them radially. For example, an axial force may be generated when the expanding enclosure contacts surfaces 327, 329 of retention members 328, 330. Once retention members are radially extended within a cavity of a mammal, proximal motion of catheter 320 is thereby inhibited. Proximal portion 324 of catheter 320 may include spatial markers so that retention members 328, 330 may be opened in a known orientation within the cavity, such as in the coronal plane within the bladder of a human.

Enclosure 321 may be expanded upon injection of less than about 2 cubic centimeters of liquid therein. Enclosure 321 preferably has a maximum dimension d8 that is less than about 3 times, such as less than about 2 times a maximum radial dimension $d_{43}$ of a distal portion 327 of catheter 320. Therefore, contact of enclosure 321 with inner surfaces of the cavity preferably has essentially no tendency to retain catheter 320 therein. Rather, resistance to proximal motion of catheter 320 is preferably due essentially only to radially expanded retention members. For example, proximal surfaces 358, 360 of retention members 328, 330 may contact the inner surface of the cavity.

Catheter 320 includes a second lumen 332 running substantially along an elongate body 322 of the catheter. Lumen 332 may operate in accordance with lumen 32 of catheter 20, such as to allow urine to exit a bladder of a catheterized human. A distal end 340 of catheter 320 includes an opening 338 to lumen 332. Retention members 328, 330 may also include passages to allow fluid to communicate between the cavity and lumen 332.

An operator may release fluid from enclosure 321, such as by using a syringe to withdraw fluid from lumen 333 or simply by breaking a seal of port 323. Loss of fluid from enclosure 321 allows the enclosure to collapse so that retention members 328, 330 may return to the insertion state. Thus, catheter 320 may be withdrawn along the passage without injury to the catheterized mammal. In the event of traumatic proximal force applied to catheter 320, fluid exits from enclosure 321, such as by collapse or rupture thereof. The fluid release allows catheter 320 to withdraw without injury.

Figure 16:
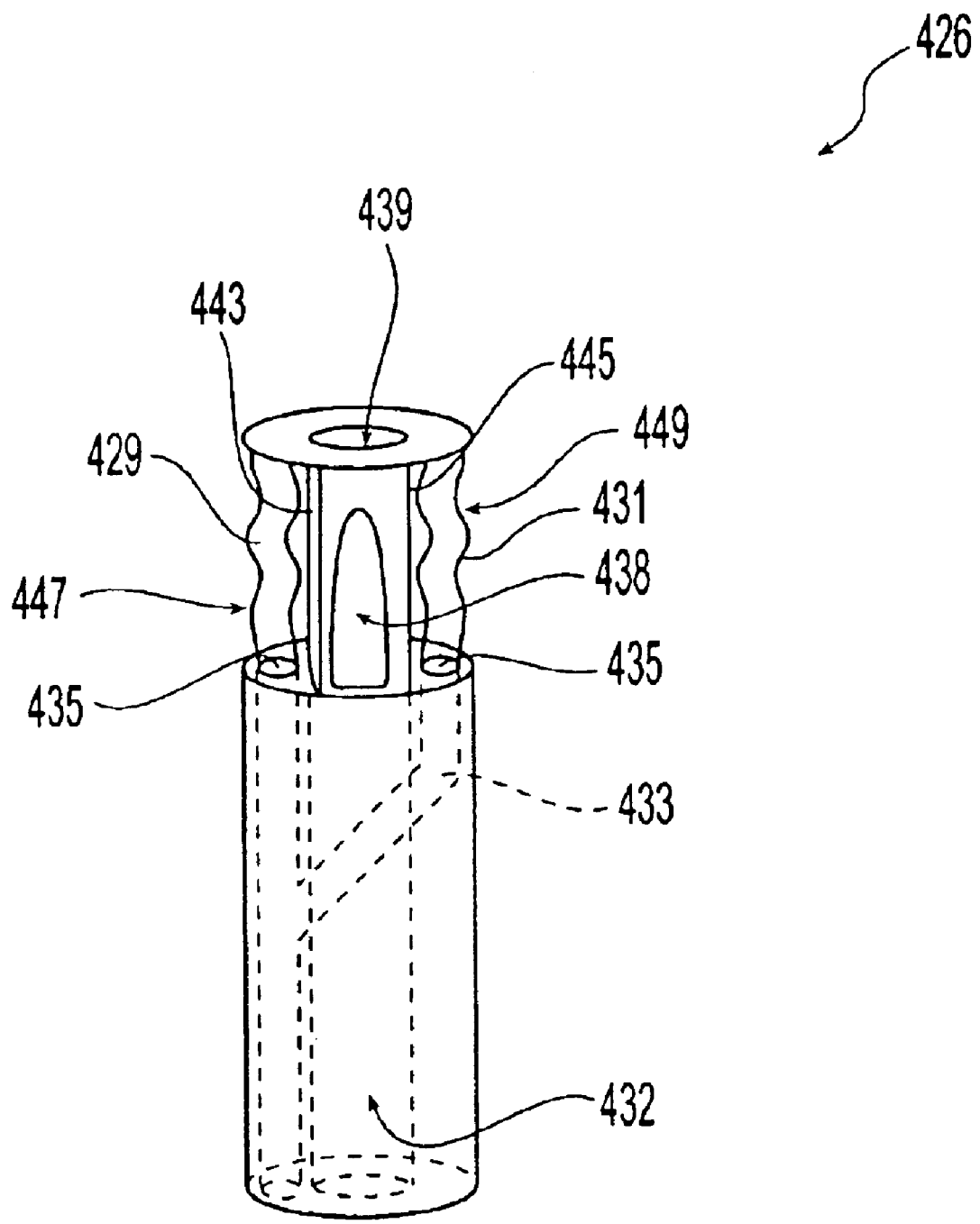
FIG. 16 shows a fifth embodiment of a catheter of the present invention, the catheter being configured in an insertion state.
Figure 17:
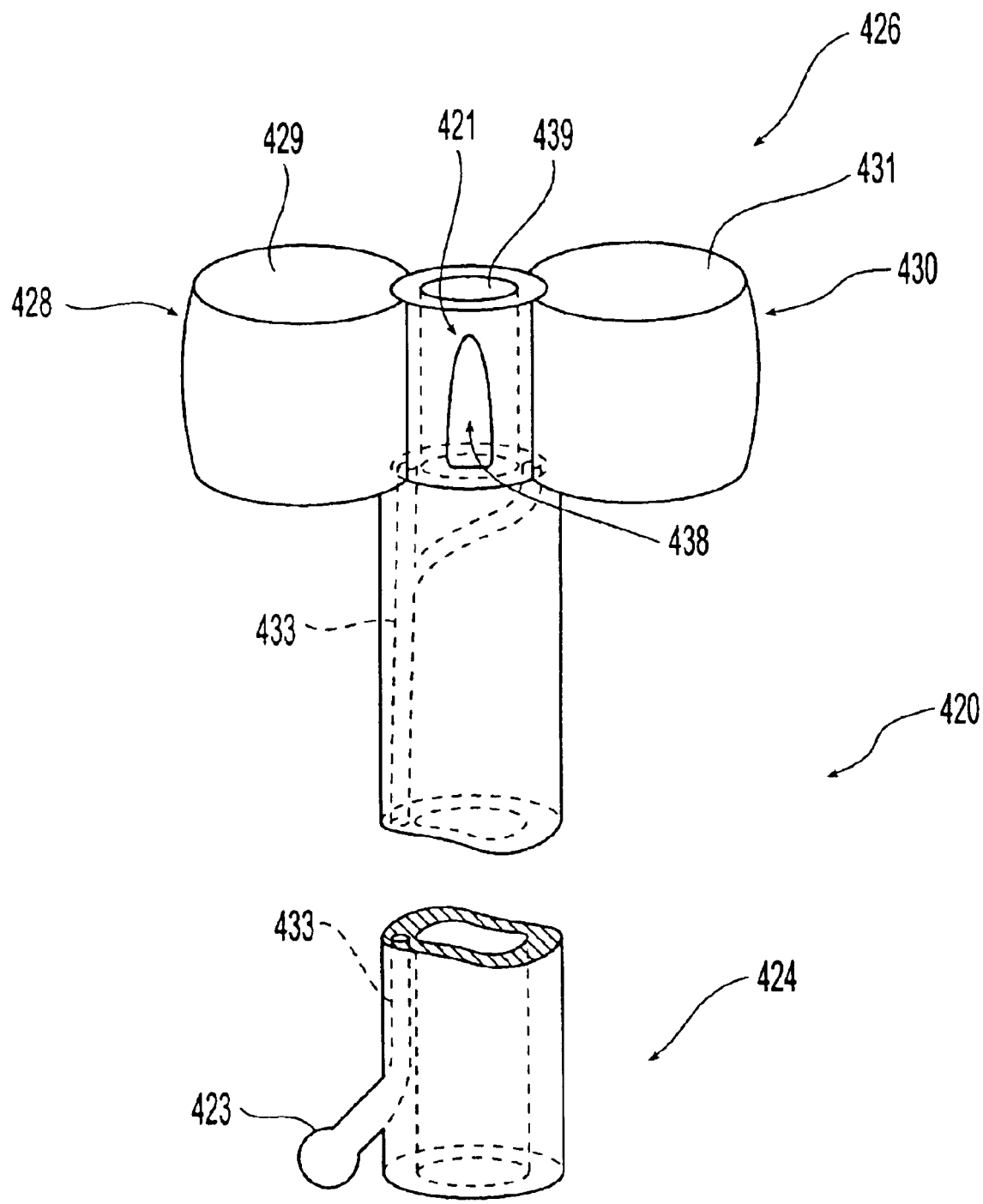
FIG. 17 shows side view of a distal portion of the catheter of FIG. 16, with the catheter being configured in a retention state.

Referring to FIGS. 16 and 17, a catheter 420 includes a distal portion 426 including first and second retention members 428, 430 comprising first and second enclosures 429, 431. In the insertion state seen in FIG. 16, the enclosures 429, 431 are substantially free of added fluid so that the enclosures do not extend radially thereby allowing catheter 420 to be inserted along a passage. In the retention state seen in FIG. 17, the enclosures included added fluid, such as a liquid, which is preferably saline. The fluid expands the enclosures 429, 431 radially, thereby extending retention members 428, 431. Proximal portion 424 of catheter 420 may include spatial markers so that retention members 428, 430 may be extended in a known orientation within the cavity, such as in the coronal plane within the bladder of a human.

A proximal portion 424 of catheter 420 includes a port 423 in fluid communication with a lumen 433, which extends from port 423 to enclosures 429, 431. Port 423 may be identical with port 333 of catheter 320 to allow introduction of fluid, such as a liquid to lumen 433. Lumen 433 may bifurcate and include openings 435 to enclosures 429, 431. Fluid entering lumen 433 enters and expands enclosures 429, 431, which extend radially. Once enclosures 429, 431 of retention members 428, 431 are radially extended within a cavity of a mammal, proximal motion of catheter 420 is thereby inhibited.

Distal portion 426 of catheter 420 includes cavities 447, 449 into which enclosures 429, 431 may collapse when in the insertion state. Respective walls 443, 445 separate cavities 447, 449 from lumen 432. Enclosures 429, 431 may be formed of material such as plastic or other polymer. Enclosures 429, 431 may be secured to catheter 420, such as by adhesive or by ultrasonic welding.

Catheter 420 includes a second lumen 432 running substantially along an elongate body 422 of the catheter. Lumen 432 may operate in accordance with lumen 32 of catheter 20, such as to allow urine to exit a bladder of a catheterized human. A distal surface 441 of catheter 420 includes an opening 438 to lumen 432. An opening 439 may be provided at a distal end 436 of catheter 420.

Figure 18:
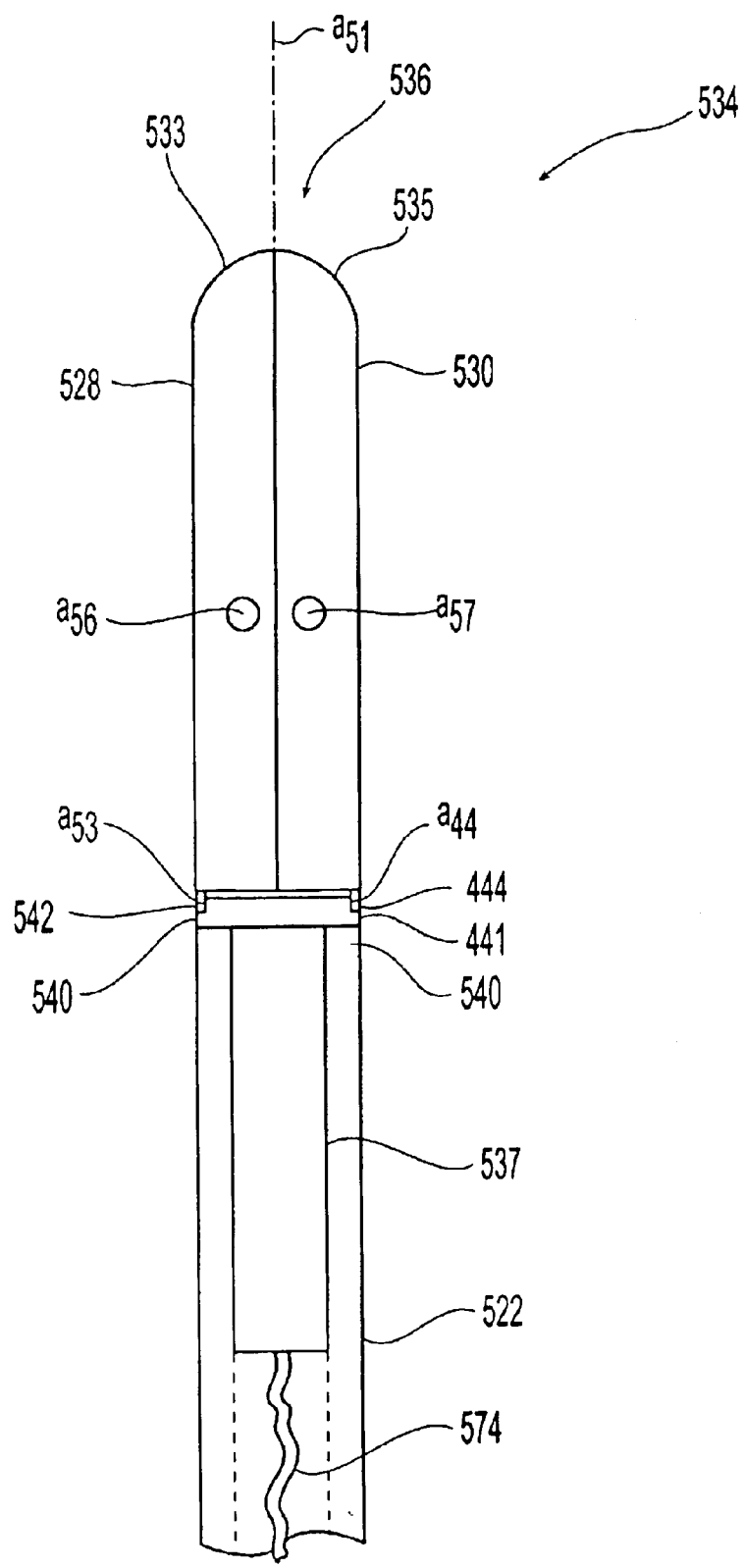
FIG. 18 shows an embodiment of a catheter retention device of the present invention, the retention device being configured in an insertion state.
Figure 19:
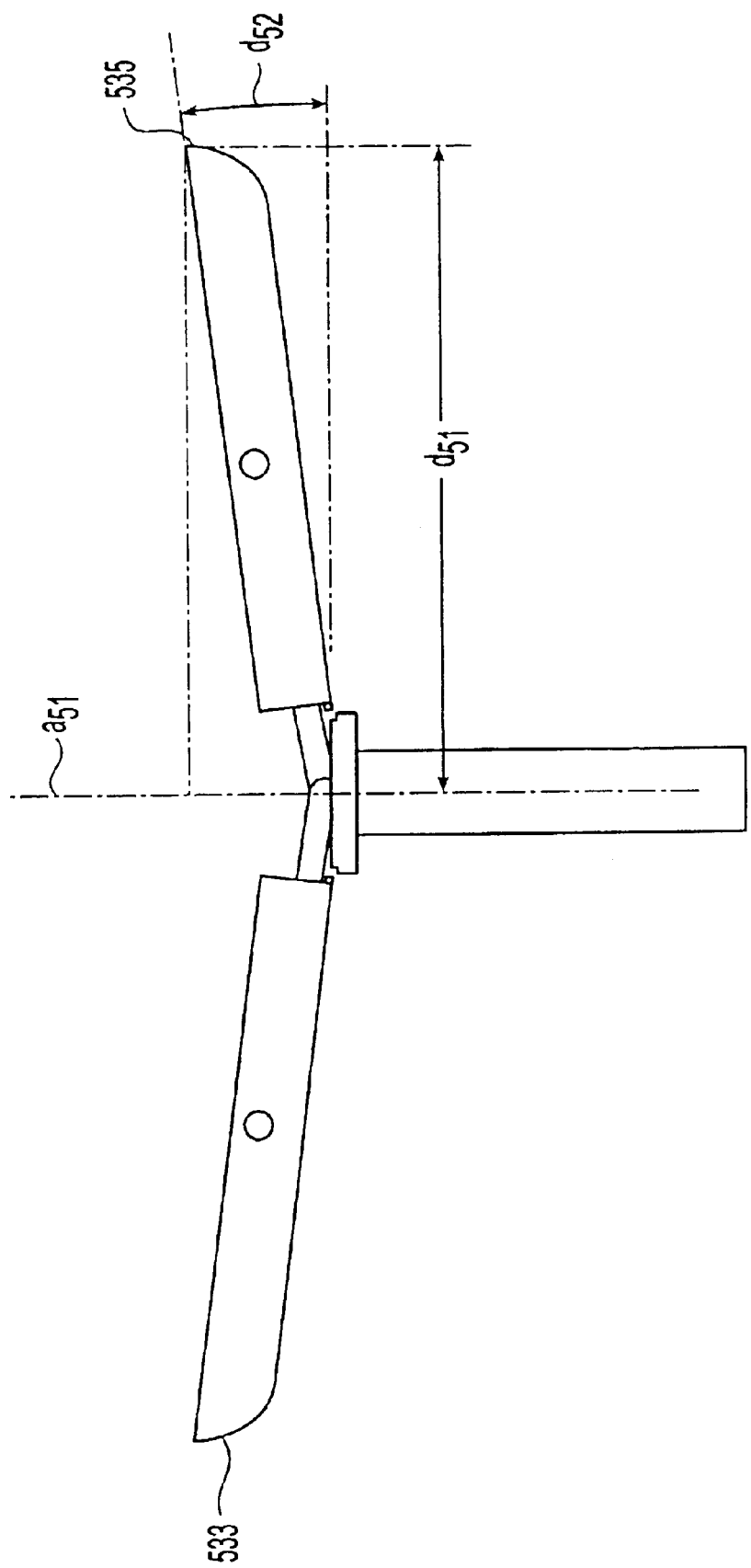
FIG. 19 shows a side view of the catheter retention device of FIG. 18, the catheter device being configured in a retention state.
Figure 20:
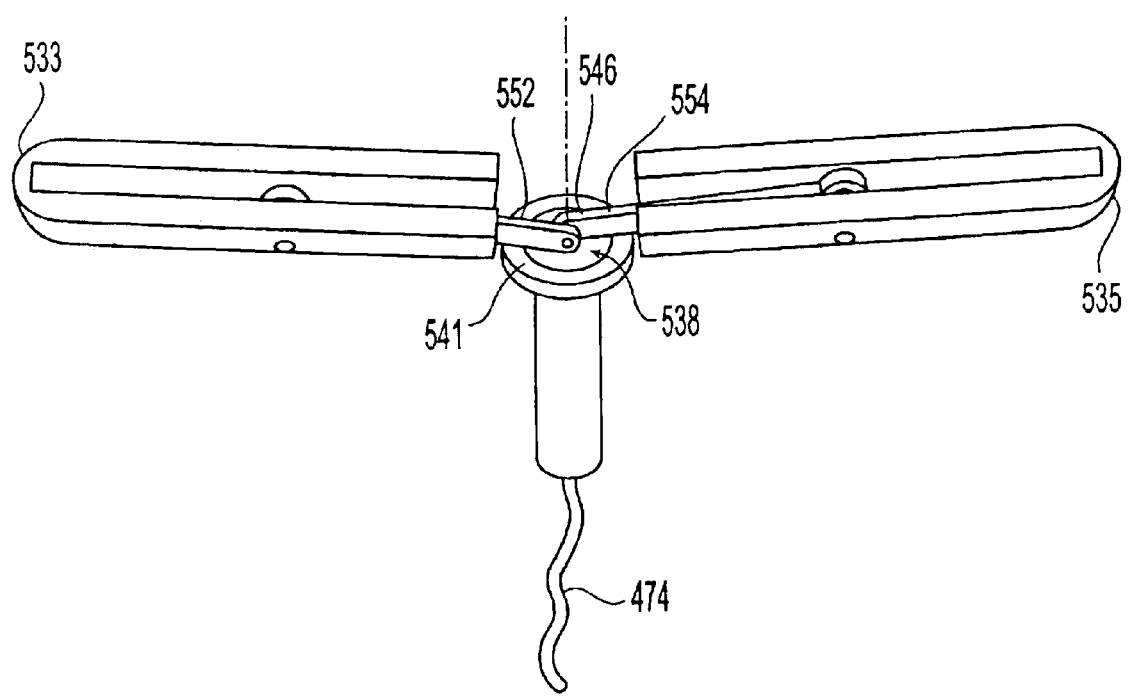
FIG. 20 shows a perspective view of the catheter retention device of FIG. 18, the catheter being configured in a retention state.

Referring to FIGS. 18–20, a catheter retention device 533 is configured to be operatively secured to an elongate body 522 to provide a catheter that may be inserted along a passage of an animal so that the catheter retention device resides within a cavity of the mammal. The elongate body is preferably a flexible member defining at least one lumen 532 therealong. Suitable flexible members include tubing formed of medical grade rubber, plastic or other polymers. Once inserted, the catheter retention device 533 may be moved to a retention state, which resists proximal motion of the associated elongate body along the passage. The retention device 533 is preferably a urinary catheter retention device configured for insertion along a urethra to a bladder of a human.

Retention device 533 includes a base 541, which is associated with a distal end 440 of the elongate body 522. To increase the association of retention device 533 and elongate body 522, a proximal extension 537 of retention device 533 may extend along a lumen 532 of elongate body 522. A distal opening 538 of base 541 allows fluid to pass between the cavity and lumen 532 of elongate body 522. At least one of base 541 and extension 537 may be secured to elongate body 522. For example, catheter retention device 533 may be secured to the elongate body 522 using, for example, adhesives or ultrasonic welding.

Retention device 533 includes at least first and second retention members 528, 530, which may be similar or identical with other described retention members of catheters in accordance with the present invention. Thus, in the insertion state, retention members 528, 530 form a distal body 534 defining a central axis $a_{51}$. Retention members 528, 530 are movably associated with retention device 533. Preferably, retention members are rotatably associated with base 441 of retention member device 533 so that, in the retention state, distal ends 533, 535 of retention members 528, 530 extend radially from central axis $a_{51}$.

Retention members 528, 530 of retention device 533 may be actuated similarly or identically with other described retention members of catheters in accordance with the present invention. For example, retention device 533 may include a linkage 546 having first and second linkage members 552, 554. A tension member 574 may be used to actuate linkage 546 by applying a proximal tension thereto so that retention device moves from an insertion state seen in FIG. 18 to a retention state seen in FIGS. 19 and 20. Retention members of catheter retention devices of the invention are configured to resist proximal motion of the associated catheter in the absence of traumatic proximal forces. In response to a traumatic proximal force, the retention members are configured to return to the insertion state to allow withdrawal with a reduced risk of injury to the catheterized individual.

Referring to FIGS. 21 and 22, a catheter 620 includes a distal portion 626 having a yoke 623, which operably supports a retention member 628. An elongate body 622, which extends proximally from distal portion 626, includes a lumen 632. An opening 638 allows fluid to enter lumen 632, pass therealong, and exit catheter 620 at a proximal portion 624 thereof.

In an insertion state, seen in FIGS. 21 and 22, retention member 628 is generally aligned with a central axis $a_{62}$ of a distal portion 627 of elongate body 622 and at least partially enclosed by yoke 623. For example, a portion of retention member 628 may be accommodated by a cavity 635 of yoke 623. Thus, catheter 620 may be inserted along a passageway of a mammal until retention member 628 is disposed within a cavity of the mammal. As discussed below, an operator may selective move the retention member 628 to a retention state, in which first and second ends 629, 631 of retention member 628 are spaced apart radially from axis $a_{62}$ thereby resisting proximal motion of the catheter 620 along the passageway. When retention member is disposed in the retention state in a cavity, such as a bladder, opening 638 is in fluid communication with the cavity so that fluid may exit the cavity through lumen 632 of catheter 620.

Retention member 628 is preferably rotatably associated with yoke 623. For example, retention member 628 may rotate about a pivot point 638 with respect to yoke 623. Pivot point 638 may be aligned with a rotation axis $a_{63}$ of retention member 728. Thus, in moving between the insertion state and the retention state, retention member 628 may rotate with respect to axis $a_{62}$ about rotation axis $a_{63}$, which may be disposed along retention member 628 between first and second ends 629, 631. Axis $a_{63}$ is preferably but is not required to be disposed substantially central to first and second ends 629, 631.

A tension member 640 may be used to actuate movement of the retention member 628 between the insertion and retention states. Tension member 640 may be secured to retention member 628 at a point 642, which is spaced apart radially from pivot point 638. Thus, when tension is communicated through tension member 640 to retention member 628, the latter rotates about pivot point 638 thereby moving from the insertion state to the retention state. To withdraw catheter 720, a stylet or trocar may be inserted along lumen 632 to push against a distal surface 644 of retention member 628 thereby urging the retention member to return to the insertion state.

Figure 25:
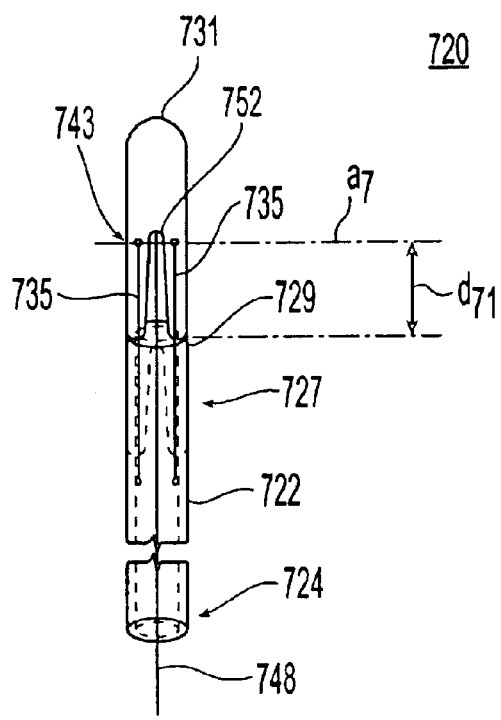
FIGS. 25 and 26 show a seventh embodiment of a catheter of the invention, with the catheter being respectively configured in an insertion state and a retention state.
Figure 26:
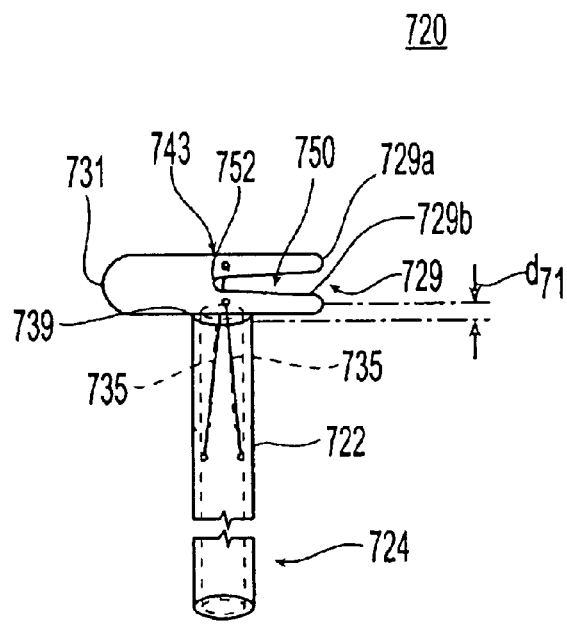

Referring to FIGS. 25 and 26, a catheter 720 includes a retention member 728 and an elongate body 722 having a proximal portion 724 and a distal portion 727. A lumen 732 extends generally along elongate body 722. An opening 738 provides passage for fluid to enter lumen 732 at distal portion 727 of elongate body 722 and pass along lumen 732 to proximal portion 724.

Retention member 728 includes first and second ends 729, 731. In an insertion state, shown in FIG. 25, first and second ends 729, 731 are generally aligned with elongate body 722 to allow insertion thereof along a passageway, such as a urethra, of a mammal. First end 729 may be bifurcated so as to include spaced apart end first ends 729a, 729b. In a retention state, shown in FIG. 26, first and second ends 729, 731 are radially spaced apart from elongate body 722 to thereby resist proximal movement of catheter 720 along the passageway.

Retention member 728 is associated with distal portion 727 of elongate body 722 by one and preferably at least two tension members 735. Tension members 735 are preferably secured to elongate body 722 and to a medial portion 743 of retention member 728. Tension members 735 are preferably elastic and, in the insertion state, urge retention member 728, via the medial portion 743, toward a distal end 739 of elongate body 722. Because first ends 729a, 729b are preferably arcuate or canted to one side, the action of tension members 735 causes retention member 728 to rotate about a medially disposed axis $a_7$ thereof. The rotation of retention member 728 draws medial portion 743 further toward a distal end of elongate body 722 thereby causing first and second ends 729, 731 to extend radially from elongate body 722 so that catheter 720 assumes a retention state as shown in FIG. 26. Because the medial portion 743 moves toward the elongate body 722 upon moving from the insertion state to the retention state, an axial distance $d_{71}$ between the generally medial portion of the retention member and distal end 739 of the elongate body decreases by at least about one half upon moving from the insertion state to the retention state.

To insert or withdraw catheter 720 along a passageway, such as a urethra, an operator may insert a stylet 748 or trocar along lumen 732 of the catheter until a distal end of the stylet 748 or trocar reaches a notch 750 of retention member 728. A distal end 752 of notch is preferably aligned with or distal to medial portion 743. Thus, as stylet 748 presses against distal end 752 of notch 750, retention member 728 assumes an insertion state as shown in FIG. 25 thereby allowing catheter 720 to be inserted or withdrawn along a passageway.

Once the catheter 720 has been inserted along a passageway so that opening 738 of lumen 732 is in fluid contact with a cavity, the operator may remove stylet 748 thereby allowing catheter 720 to return to the retention state.

Figure 27:
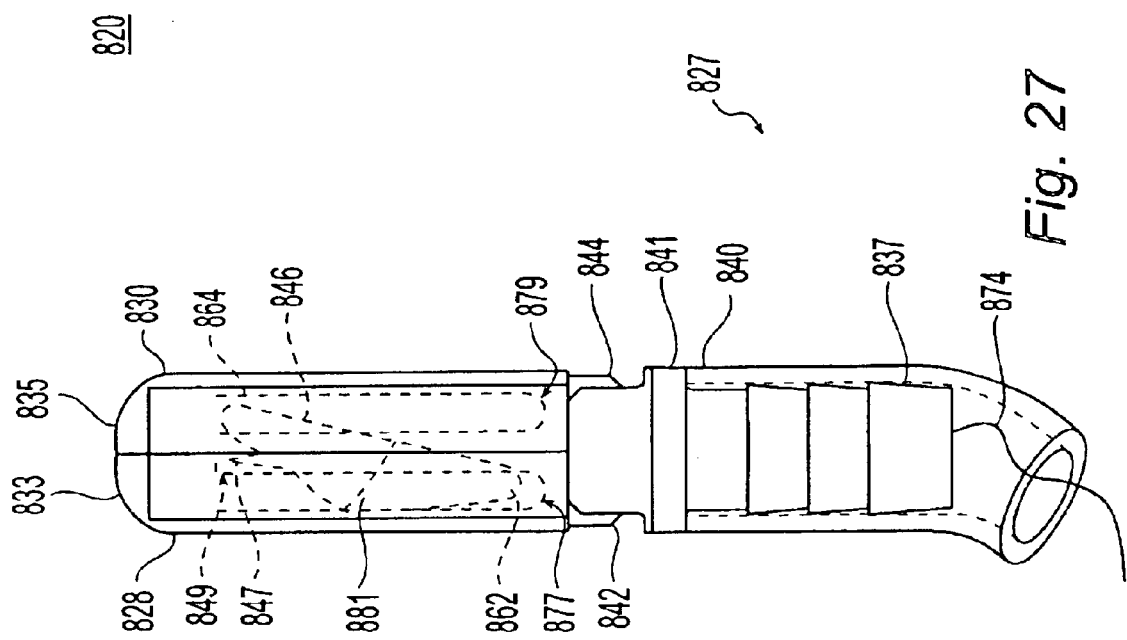
FIG. 27 shows an eighth embodiment of a catheter of the invention, with the catheter being configured in an insertion state.
Figure 28:
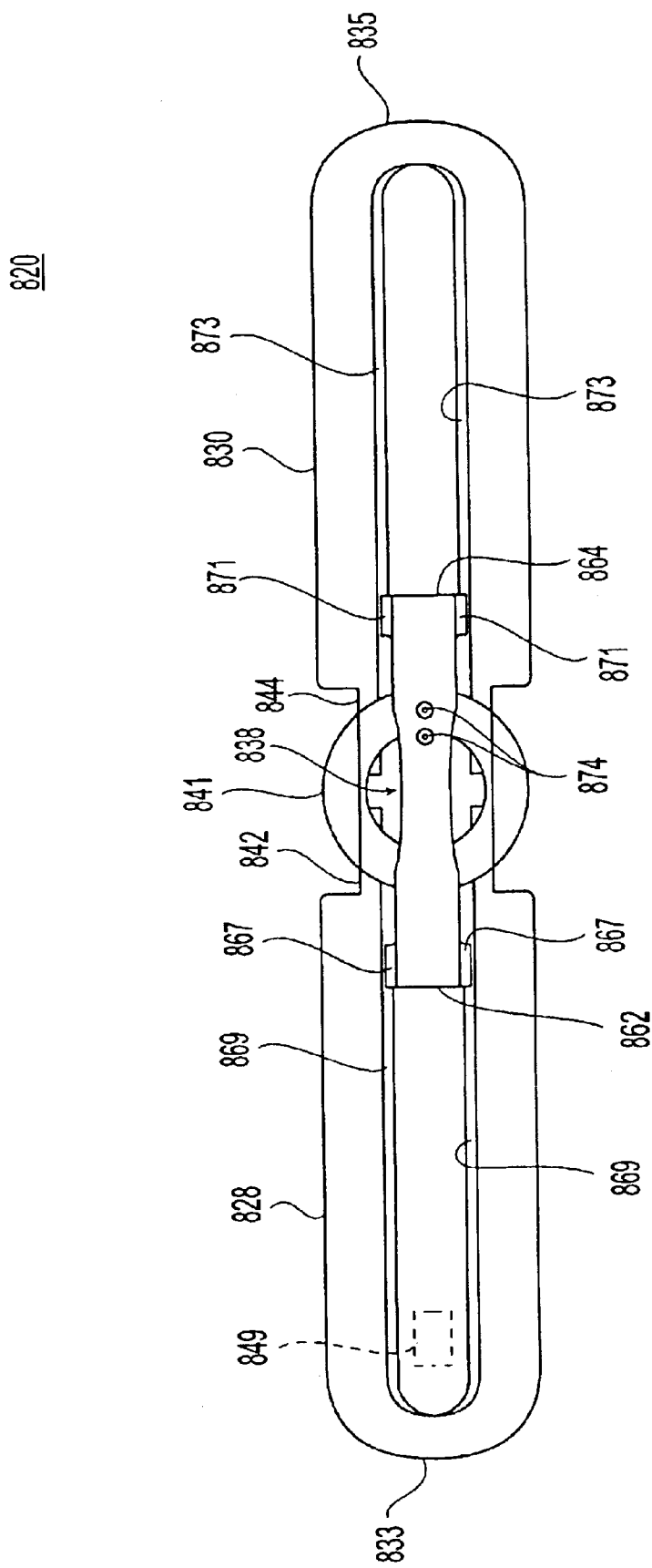
FIGS. 28 and 29 show the catheter of FIG. 27 but being configured in a retention state.
Figure 29:
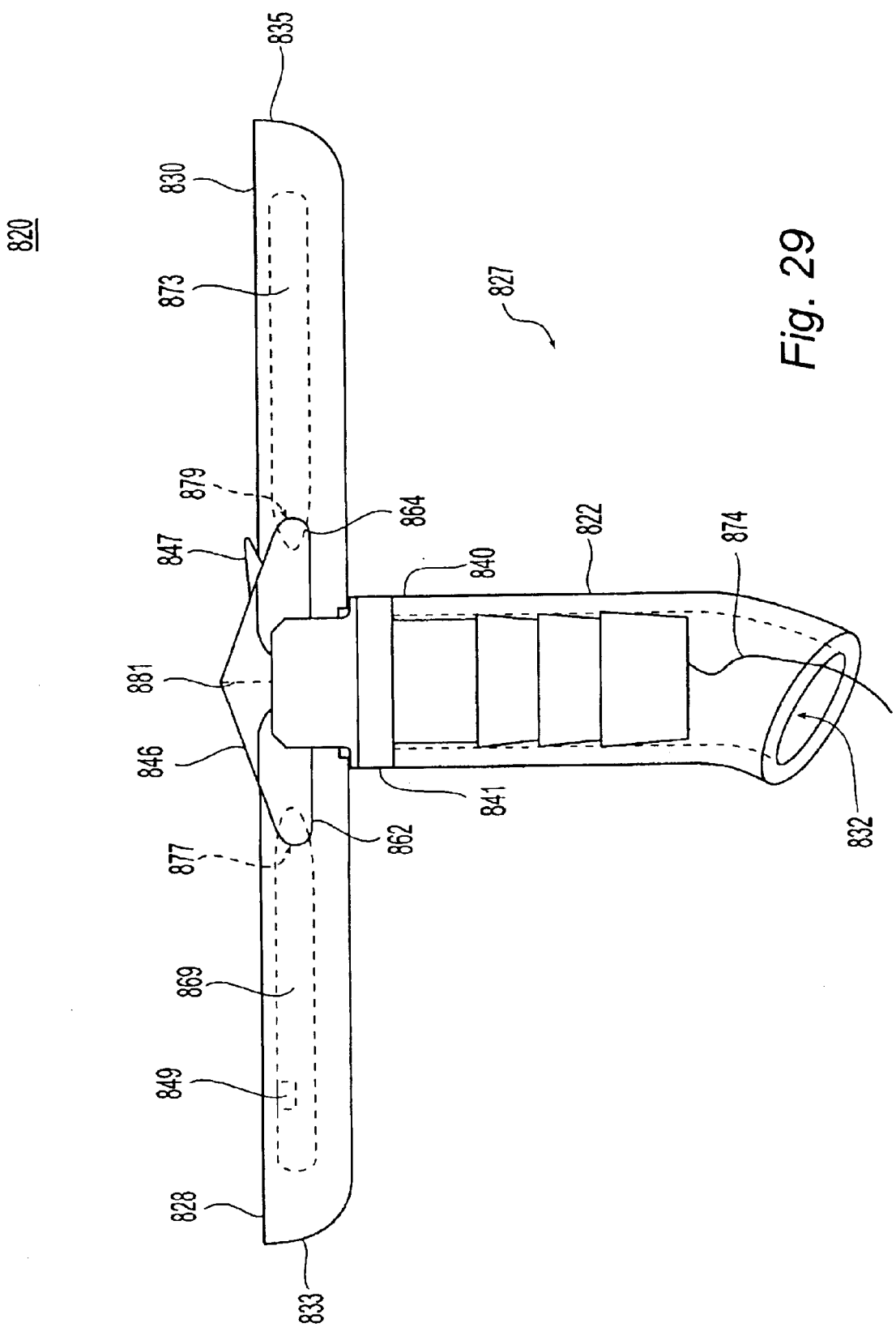

Referring to FIGS. 27–29, a catheter 820 includes first and second retention members 828, 830 moveably associated therewith. Catheter 820 also includes an elongate body 822, which may have a lumen 832 therethrough in accordance with the elongate bodies of other catheters discussed herein. For example, lumen 832 may provide a passage for fluid from a distal portion 827 of elongate body to a proximal portion of the elongate body. Only a distal portion 827 of elongate body 822 is shown in FIGS. 27–29. It should be understood, however, that elongate body 822 may be similar or identical to elongate bodies of other catheters discussed herein.

Catheter 820 may include a base 841, which is associated with a distal end 840 of the elongate body 822. A proximal extension 837 may extend partially along lumen 832 from base 841. A distal opening 838 of base 841 allows fluid to pass between a body cavity and lumen 832. At least one of base 841 and extension 837 may be secured to elongate body 822. For example, base 841 and/or extension 837 may be secured to the elongate body 822 using, for example, adhesives or ultrasonic welding.

First and second retention members 828, 830 are preferably rotatably associated with catheter 820. In the embodiment of FIGS. 27–29, retention members 828, 830 are rotatably associated with base 841 by flexible connections 842, 844. Alternatively, the rotatable association may be accomplished by other elements, such as pivots or ball and socket joints.

A linkage member 846 is operatively associated with the first and second retention members 828, 830. In an insertion state, as shown in FIG. 27, the linkage member 846 inhibits the retention members 828, 830 from moving apart as toward a retention state. Linkage member 846 may be actuated by an actuation member 874 to actuate movement of retention members 828, 830 from the insertion state to the retention state. In a retention state, as shown in FIGS. 28, 29, the linkage member 846 inhibits the retention members 828, 830 from moving toward one another as toward an insertion state. Thus, in the retention state, retention members 828, 830 may operate to retain a catheter in a body cavity in accordance with other retention members discussed herein. Preferably, the body cavity is a bladder and retention of the catheter 820 provides fluid contact between the bladder and an opening 838 to lumen 832.

A first linkage end 862 of linkage member 846 is both rotatably and slidably associated with retention member 828. First linkage end 862 may include projections 867 that engage retention member 828, as by engaging a track 869 therealong. A second linkage end 864 of linkage member 846 is both rotatably and slidably associated with retention member 830. Second linkage end 864 may include projections 871 that engage retention member 830, as by engaging a track 873 therealong.

When retention members are disposed in the insertion state shown in FIGS. 27, 28, a projection 847 of linkage member 846 engages a notch 849 of retention member 828 thereby preventing distal ends 833, 835 of retention members 828, 830 from moving apart radially with respect to one another. Actuation of linkage member 846 via actuation member 874 preferably slides linkage member 846 longitudinally with respect to retention members 828, 830 to thereby disengage linkage member projection 847 and retention member notch 849. For example, linkage member 846 may be actuated by applying tension to actuation member 874 thereby sliding linkage member 846 proximally along tracks 869, 873 in the direction of arrows 875 seen in FIG. 27.

Upon disengagement of projection 847 and notch 849, distal retention member ends 833, 835 may move radially with respect to one another toward the retention state shown in FIGS. 28, 29. As distal retention member ends 833, 835 move radially, retention member 828 rotates with respect to first linkage member end 862 and retention member 830 rotates with respect to second linkage member end 864. First and second linkage member ends 862, 864 may continue to slide with respect to retention members 828, 830 as the retention members move toward the retention state.

When in the retention state, as seen in FIGS. 28, 29, projections 867 of first linkage member end 862 engage narrowed portions 877 of tracks 869 and projections 871 of second linkage member end 864 engage narrowed portions 879 of tracks 873. The engagement of projections 867, 871 and respective narrowed portions 877, 879 inhibits linkage member 846 from sliding with respect to retention members 828, 830 thereby inhibiting the retention members from returning to the insertion state. Thus, when retention members 828, 830 are disposed in a body cavity in the retention state, the retention members will be retained in the body cavity absent a traumatic force applied to the retention members.

When in the retention state within a body cavity, linkage member 846 and retention members 828, 830 preferably resist proximal movement of catheter 832 for proximally applied forces of less than about 12 Newtons, such as less than about 10 Newtons, for example, less than about 8 Newtons, applied to elongate body 22, but return to an insertion state to permit injury free withdrawal of catheter 20 upon application of a force less than about 25 Newtons, such as a force of less than about 20 Newtons, for example, a force of less than about 15 Newtons.

Upon application of a traumatic force, return to an insertion state may be facilitated by a disengagement of linkage member 846 and narrowed portions 877, 879 of retention members 828, 830. Alternatively, linkage member 846 may include a weakened portion, which may be a cut 881 partially through the linkage member 846. Upon the application of a traumatic force to catheter 820 in the retention state, linkage member 846 changes shape, such as by folding about cut 881, thereby allowing retention members 828, 830 to move toward the insertion state and withdraw without injury to the catheterized individual. Retention members 828, 830 may also be returned to the insertion state by inserting a trocar or stylet along lumen 832 to disengage first and second ends 862, 864 of linkage member 846 from narrowed portions of retention members 828, 830 and/or to change the shape of linkage member 846, such as by flexing about cut 881.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A catheter, comprising:
an elongate body having distal and proximal ends, the elongate body having at least one lumen therethrough, a distal portion of the elongate body having a perimeter;
first and second retention members;
a linkage comprising a linkage member operably associated with the first retention member, with the first and second retention members being actuated by the linkage to be selectively disposed in either an insertion state or a retention state, wherein:
in the insertion state, the first and second retention members forming a distal body defining a central axis, the central axis being generally spaced apart from the perimeter of the distal portion of the elongate body, the distal body and elongate body insertable along a passageway of a mammal; and
in the retention state, the first and second retention members are selectively disposed in a spaced apart configuration to resist proximal movement of the catheter along the passageway of the mammal, with the linkage member being disposed along the first retention member;
wherein the distal body bifurcates upon moving from the insertion state to the retention state; and
wherein the catheter further comprises a proximal portion having at least one spatial marker indicative of an orientation of the first and second retention members.

2. The catheter of claim 1, wherein the at least one spatial marker is indicative of whether the retention members are aligned with a coronal plane of a human catheterized with the catheter.

3. A method for catheterizing a mammal, comprising:
providing the catheter of claim 1;
inserting the catheter along a passageway of the mammal until the first and second retention members of the catheter enter a cavity of the mammal; and
moving the retention members from the insertion state to the retention state, whereby the first and second retention members are removably retained within the cavity.

4. A catheter, comprising:
an elongate body having distal and proximal ends, the elongate body having at least one lumen therethrough, a distal portion of the elongate body having a perimeter;
first and second retention members;
a linkage comprising a linkage member operably associated with the first retention member, with the first and second retention members being actuated by the linkage to be selectively disposed in either an insertion state or a retention state, wherein:
in the insertion state, the first and second retention members forming a distal body defining a central axis, the central axis being generally spaced apart from the perimeter of the distal portion of the elongate body, the distal body and elongate body insertable along a passageway of a mammal;
in the retention state, the first and second retention members are selectively disposed in a spaced apart configuration to resist proximal movement of the catheter along the passageway of the mammal, with the linkage member being disposed along the first retention member;
wherein the distal body bifurcates upon moving from the insertion state to the retention state; and
wherein the first and second retention members each include proximal and distal ends, the proximal ends rotatably associated with the distal end of the elongate body.

5. The catheter of claim 4, wherein the distal ends of the retention members are free ends.

6. The catheter of claim 4, wherein the distal end of at least one of the first and second retention members rotates about a rotation axis with respect to the distal end of the elongate body, the rotation axis generally disposed at a proximal end of the retention member.

7. The catheter of claim 6, wherein the distal end of each of the first and second retention members rotate about a respective rotation axis with respect to the distal end of the elongate body, the rotation axes being generally disposed at the respective proximal ends of the retention members.

8. The catheter of claim 6, wherein a respective contour of the first and second retention members remains substantially constant upon movement from the insertion state to the retention state.

9. The catheter of claim 4, wherein the distal end of the catheter includes an opening to the lumen, wherein the central axis of the distal portion of the elongate body intersects the opening.

10. The catheter of claim 4, wherein an inner surface of the lumen is substantially concentric with an outer surface of the elongate body.

11. The catheter of claim 4, wherein, when the first and second retention members are in the retention state, a distance between a distal extent of the retention members and an opening to the lumen of the elongate body is less than about 3 times a maximum radial dimension of the lumen, wherein the distance is taken along the central axis of the distal portion of the elongate body.

12. The catheter of claim 4, wherein, the first and second retention members move proximally upon moving from the insertion state to the retention state.

13. A catheter, comprising:

an elongate body having distal and proximal ends, the elongate body having at least one lumen therethrough, a distal portion of the elongate body having a perimeter;

first and second retention members, the first and second retention members being selectively disposed in either an insertion state or a retention state, wherein:

in the insertion state, the first and second retention members forming a distal body defining a central axis, the central axis being generally spaced apart from the perimeter of the distal portion of the elongate body, the distal body and elongate body insertable along a passageway of a mammal; and in the retention state, the first and second retention members are selectively disposed in a spaced apart configuration to resist proximal movement of the catheter along the passageway of the mammal;

wherein the first and second retention members each include proximal and distal ends, the proximal ends rotatably associated with the distal end of the elongate body; and wherein, in the insertion state, a distal portion of the first retention member extends beyond the second retention member, the distal portion of the first retention member having a substantially unbroken surface.

14. The catheter of claim 13, wherein, when viewed along the central axis of the distal body, the substantially unbroken surface of the first retention member obscures at least a portion of the second retention member.

15. A catheter, comprising:

an elongate body having distal and proximal ends, the elongate body having at least one lumen therethrough, a distal portion of the elongate body having a perimeter;

first and second retention members, the first and second retention members being selectively disposed in either an insertion state or a retention state, wherein:

in the insertion state, the first and second retention members forming a distal body defining a central axis, the central axis being generally spaced apart from the perimeter of the distal portion of the elongate body, the distal body and elongate body insertable along a passageway of a mammal; and in the retention state, the first and second retention members are selectively disposed in a spaced apart configuration to resist proximal movement of the catheter along the passageway of the mammal; and a linkage, wherein the first and second retention members are actuated via the linkage and wherein the linkage comprises a linkage member, the linkage member being rotatably associated with the first retention member and slidably associated with the second retention member.

16. The catheter of claim 15, wherein the second retention member includes a stop, which, in the retention state, releasably accommodates an end of the linkage member thereby inhibiting the retention members from returning to the insertion state.

17. The catheter of claim 16, wherein the stop and the end of the linkage member are configured to dissociate in response to a predetermined proximal force so that the retention members may return to the insertion state.

18. A catheter, comprising:

an elongate body having distal and proximal ends, the elongate body having at least one lumen therethrough, a distal portion of the elongate body having a perimeter;

first and second retention members, the first and second retention members being selectively disposed in either an insertion state or a retention state, wherein:

in the insertion state, the first and second retention members forming a distal body defining a central axis, the central axis being generally spaced apart from the perimeter of the distal portion of the elongate body, the distal body and elongate body insertable along a passageway of a mammal; and in the retention state, the first and second retention members are selectively disposed in a spaced apart configuration to resist proximal movement of the catheter along the passageway of the mammal; and a linkage, wherein the first and second retention members are actuated via the linkage and wherein the linkage includes first and second linkage members having respective first and second ends, wherein the first end of the first linkage member is rotatably associated with the first retention member, the first end of the second linkage member is rotatably associated with the second retention member, and the respective second ends of the first and second linkage members are rotatably associated with one another.

19. A catheter, comprising:

an elongate body having distal and proximal ends, the elongate body having at least one lumen therethrough, a distal portion of the elongate body having a perimeter;

first and second retention members, the first and second retention members being selectively disposed in either an insertion state or a retention state, wherein:

in the insertion state, the first and second retention members forming a distal body defining a central axis, the central axis being generally spaced apart from the perimeter of the distal portion of the elongate body, the distal body and elongate body insertable along a passageway of a mammal; and in the retention state, the first and second retention members are selectively disposed in a spaced apart configuration to resist proximal movement of the catheter along the passageway of the mammal; and a linkage, wherein the first and second retention members are actuated via the linkage and wherein the linkage comprises first and second linkage members, the first and second linkage members rotatable with respect to one another about a rotation axis, wherein, as the first and second retention members move between the insertion state and the retention state, the rotation axis translates substantially along the central axis of the distal body.

20. The catheter of claim 19, wherein, in the insertion state, a distal extent of at least one of the first and second retention members is greater than a distal extent of the linkage.

21. A catheter, comprising:

an elongate body having distal and proximal ends, the elongate body having at least one lumen therethrough, a distal portion of the elongate body having a perimeter;

first and second retention members, the first and second retention members being selectively disposed in either an insertion state or a retention state, wherein:

in the insertion state, the first and second retention members forming a distal body defining a central axis, the central axis being generally spaced apart from the perimeter of the distal portion of the elongate body, the distal body and elongate body insertable along a passageway of a mammal; and in the retention state, the first and second retention members are selectively disposed in a spaced apart configuration to resist proximal movement of the catheter along the passageway of the mammal; and a linkage, wherein the first and second retention members are actuated via the linkage and wherein the linkage includes a linkage member having first and second linkage member ends, the first linkage member end is slidably and rotatably associated with the first retention member and the second linkage member end is slidably and rotatably associated with the second retention member.

22. A catheter, comprising:

an elongate body having distal and proximal ends, the elongate body having at least one lumen therethrough, a distal portion of the elongate body having a perimeter;

first and second retention members, the first and second retention members being selectively disposed in either an insertion state or a retention state, wherein:

in the insertion state, the first and second retention members forming a distal body defining a central axis, the central axis being generally spaced apart from the perimeter of the distal portion of the elongate body, the distal body and elongate body insertable along a passageway of a mammal; and in the retention state, the first and second retention members are selectively disposed in a spaced apart configuration to resist proximal movement of the catheter along the passageway of the mammal;

wherein the catheter includes a flexible enclosure, and wherein movement from the insertion state to the retention state is actuated by expansion of the flexible enclosure.

23. A catheter, comprising:

an elongate body having distal and proximal ends, the elongate body having at least one lumen therethrough, a distal portion of the elongate body having a perimeter;

first and second retention members, the first and second retention members being selectively disposed in either an insertion state or a retention state, wherein:

in the insertion state, the first and second retention members forming a distal body defining a central axis, the central axis being generally spaced apart from the perimeter of the distal portion of the elongate body, the distal body and elongate body insertable along a passageway of a mammal; and in the retention state, the first and second retention members are selectively disposed in a spaced apart configuration to resist proximal movement of the catheter along the passageway of the mammal;

wherein, in the retention state, a radial extent of at least one of the first and second retention members is at least about as great as a length of the retention member.

24. A catheter, comprising:

an elongate body having distal and proximal ends, the elongate body having at least one lumen therethrough, a distal portion of the elongate body having a perimeter;

first and second retention members, the first and second retention members being selectively disposed in either an insertion state or a retention state, wherein:

in the insertion state, the first and second retention members forming a distal body defining a central axis, the central axis being generally spaced apart from the perimeter of the distal portion of the elongate body, the distal body and elongate body insertable along a passageway of a mammal; and in the retention state, the first and second retention members are selectively disposed in a spaced apart configuration to resist proximal movement of the catheter along the passageway of the mammal;

wherein the distal body bifurcates upon moving from the insertion state to the retention state; and wherein the catheter further comprises a proximal portion having at least one spatial marker indicative of an orientation of the first and second retention members.

25. The catheter of claim 24, wherein the at least one spatial marker is indicative of whether the retention members are aligned with a coronal plane of a human catheterized with the catheter.

26. A catheter, comprising:

an elongate body having distal and proximal ends, the elongate body having at least one lumen therethrough, a distal portion of the elongate body having a perimeter;

first and second retention members;

a linkage comprising a linkage member operably associated with the first retention member, with the first and second retention members being actuated by the linkage to be selectively disposed in either an insertion state or a retention state, wherein:

in the insertion state, the first and second retention members forming a distal body defining a central axis, the central axis being generally spaced apart from the perimeter of the distal portion of the elongate body, the distal body and elongate body insertable along a passageway of a mammal;

in the retention state, the first and second retention members are selectively disposed in a spaced apart configuration to resist proximal movement of the catheter along the passageway of the mammal, with the linkage member being disposed along the first retention member;

wherein the distal body bifurcates upon moving from the insertion state to the retention state; and wherein the passageway is a urethra.

27. The catheter of claim 26, wherein the mammal is a human.

28. A urethral catheter for catheterizing a bladder of a human having a coronal plane, the urethral catheter comprising:

an elongate body having a distal portion and a proximal portion, the elongate body having a passage therealong;

a distal body formed by first and second retention members;

a linkage comprising a linkage member operably associated with the first retention member, with the first and second retention members being movably associated with the distal portion of the elongate body and being actuated by the linkage to be movable between an insertion state and a retention state, wherein, in the retention state:

the first and second retention members extend radially and substantially along a single plane from the elongate body;

the linkage member is disposed proximate a region of the first retention member configured and dimensioned for receiving the linkage member; and the proximal portion of the elongate body includes at least one spatial marker indicative of whether the first and second retention members are generally aligned with the coronal plane of the human when the first and second retention members are in the bladder of the human;

wherein the distal body bifurcates upon changing from the insertion state to the retention state.

29. The urethral catheter of claim 28, wherein the first and second retention members include respective distal outer surfaces, and wherein the respective distal outer surfaces define an angle of at least about 80 degrees with respect to a central axis of the distal portion of the elongate body.

30. A urinary catheter retention device for insertion along a urethra into a bladder of a human to releasably retain a passage of an elongate body in fluid communication with the bladder, the retention device comprising:

a base operably securable to an end of the elongate body;

a distal body formed by first and second retention members;

a linkage comprising a linkage member operably associated with the first retention member, with the first and second retention members being movably associated with the base and having respective free distal ends, the free distal ends of the retention members movable and separable by the linkage to actuate between an insertion state and a retention state, wherein:

in the insertion state, the first and second retention members cooperate to form a body, the body being insertable along the urethra; and in the retention state, the free distal ends are spaced apart from one another to resist proximal movement of the elongate body with respect to the bladder, with the linkage member being disposed along a region of the first retention member configured and dimensioned to receive the linkage member;

wherein the distal body bifurcates upon moving from the insertion state to the retention state.

31. A urethral catheter, comprising:

an elongate body, the elongate body having at least one lumen therethrough;

a distal body comprising a first retention member;

a linkage comprising a linkage member pivotably associated with the first retention member, the first retention member having first and second ends and being selectively disposed in either an insertion state or a retention state through actuation of the linkage, wherein:

in the insertion state, the first and second ends of the retention member are generally aligned with the elongate body so that at least a portion of the catheter is insertable along a urethra of a mammal; and in the retention state, the first and second ends of the retention member are spaced apart from the elongate body to resist proximal movement of the retention member along the urethra of the mammal, with the linkage member being disposed along the first retention member;

wherein the distal body bifurcates upon moving from the insertion state to the retention state.

32. The catheter of claim 31, wherein the catheter includes at least one tension member that urges a generally medial portion of the retention member toward a distal end of the catheter.

33. The catheter of claim 32, wherein an axial distance between the generally medial portion of the retention member and a distal end of the elongate body decreases by at least about one half upon moving from the insertion state to the retention state.

34. A urethral catheter, comprising:

an elongate body, the elongate body having at least one lumen therethrough;

a first retention member, the first retention member having first and second ends and being selectively disposed in either an insertion state or a retention state, wherein:

in the insertion state, the first and second ends of the retention member are generally aligned with the elongate body so that at least a portion of the catheter is insertable along a urethra of a mammal; and in the retention state, the first and second ends of the retention member are spaced apart from the elongate body to resist proximal movement of the retention member along the urethra of the mammal;

wherein a generally medial portion of the retention member is rotatably associated with the catheter.

35. A urethral catheter, comprising:

an elongate body having a distal end and a proximal end and at least one lumen therethrough;

a distal body comprising at least one retention member, the at least one retention member being generally associated with the distal end of the elongate body and selectively actuable in at least an insertion state and a retention state;

a linkage comprising a linkage member operably associated with the at least one retention member for actuating the at least one retention member, wherein:

in the insertion state, the at least one retention member is generally aligned with the elongate body and insertable along a urethra of a mammal; and in the retention state, at least a portion of the at least one retention member is radially spaced apart from the elongate body, with the linkage member being disposed along a region of the at least one retention member configured and dimensioned to receive the linkage member;

wherein the distal body bifurcates upon moving from the insertion state to the retention state; and wherein, upon the application of a force of less than about 12 Newtons directed generally proximally along the elongate body, the at least one retention member resists proximal movement of the catheter along the urethra and, upon the application of a force of more than about 12 Newtons and less than about 25 Newtons directed generally proximally along the elongate body, the at least one retention member returns to the insertion state to permit withdrawal of the catheter along the urethra.

36. The catheter of claim 35, wherein, upon the application of a force of more than about 12 Newtons and less than about 20 Newtons directed generally proximally along the elongate body, the at least one retention member returns to the insertion state to permit withdrawal of the catheter along the urethra.

37. The catheter of claim 35, wherein, upon the application of a force of more than about 12 Newtons and less than about 15 Newtons directed generally proximally along the elongate body, the at least one retention member returns to the insertion state to permit withdrawal of the catheter along the urethra.

38. A catheter, comprising:

an elongate body having distal and proximal ends, the elongate body having at least one lumen therethrough, a distal portion of the elongate body having a perimeter;

first and second retention members;

a linkage comprising a linkage member operably associated with the first retention member, with the first and second retention members being actuated by the linkage to be selectively disposed in either an insertion state or a retention state, wherein:

in the insertion state, the first and second retention members forming a distal body defining a central axis, the central axis being generally spaced apart from the perimeter of the distal portion of the elongate body, the distal body and elongate body insertable along a passageway of a mammal;

in the retention state, the first and second retention members are selectively disposed in a spaced apart configuration to resist proximal movement of the catheter along the passageway of the mammal, with the linkage member being disposed along the first retention member;

wherein the distal body bifurcates upon moving from the insertion state to the retention state; and wherein in the retention state the linkage member is disposed along the first retention member in a captivating region.

39. A method for selectively retaining a catheter in a urethra of a mammal to provide a drainage passage for a bladder of the mammal comprising:

extending a catheter within the urethra, the catheter comprising an elongate body with at least one lumen extending therethrough, a distal portion having first and second retention members disposed proximate an end of the elongate body and selectively configured and dimensioned for movement within the urethra, and a linkage having a linkage member operably associated with the first retention member;

actuating the linkage to bifurcate the distal portion to move the retention members within the bladder so that the retention members contact a surface of the bladder and resist movement of the catheter out of the urethra, with the linkage member being disposed along a region of the first retention member configured and dimensioned to receive the linkage member and with the at least one lumen being in fluid communication with the bladder.

40. The method of claim 39, further comprising:

actuating the linkage so that the retention members are disposed to permit movement of the catheter out of the urethra.

41. A method for selectively retaining a catheter in a urethra of a mammal to provide a drainage passage for a bladder of the mammal comprising:

extending a catheter within the urethra, the catheter comprising an elongate body with at least one lumen extending therethrough, a distal portion having first and second retention members disposed proximate an end of the elongate body and selectively configured and dimensioned for movement within the urethra, and at least one spatial marker indicative of an orientation of the first and second retention members;

using the at least one spatial marker to orient the catheter so that the retention members are aligned with a coronal plane of the mammal;

opening the distal portion to move the retention members within the bladder so that the retention members contact a surface of the bladder and resist movement of the catheter out of the urethra.

42. The method of claim 41, wherein contact between the catheter and a trigone of the mammal is avoided when the retention members contact the surface of the bladder.

43. A catheter for use in draining a bladder of a mammal comprising:

an elongate body with at least one lumen extending therethrough;

a distal portion having first and second retention members disposed proximate an end of the elongate body, the distal portion configured and dimensioned to bifurcate; and a linkage having a linkage member operably associated with the first retention member, the linkage member being operable to bifurcate the distal portion with the linkage member resting proximate a surface of the first retention member that is shaped to receive the linkage member and the retention members being radially disposed with respect to the end of the elongate body;

wherein the catheter is configured and dimensioned for extending through a urethra of the mammal.

44. The catheter of claim 43, wherein the surface of the first retention member that is shaped to receive the linkage member comprises a channel.

45. The catheter of claim 43, wherein the retention members are configured and dimensioned to contact surfaces of the bladder and resist movement of the catheter out of the urethra.

46. The catheter of claim 43, further comprising a proximal portion having at least one spatial marker indicative of an orientation of the first and second retention members.

* * * * *

UNITED STATES PATENT AND TRADEMARK OFFICE
CERTIFICATE OF CORRECTION

PATENT NO. : 6,929,621 B2 Page 1 of 1
DATED : August 16, 2005
INVENTOR(S) : Willet F. Whitmore III et al.

It is certified that error appears in the above-identified patent and that said Letters Patent is hereby corrected as shown below:

Title page,
Item [12], after "Whitmore" insert -- III --;
Item [75], Inventors, after "Whitmore" insert -- III --.

Signed and Sealed this

Eleventh Day of October , 2005

JON W. DUDAS
*Director of the United States Patent and Trademark Office*